(12) United States Patent
Sugita et al.

(10) Patent No.: US 6,572,839 B2
(45) Date of Patent: Jun. 3, 2003

(54) SENSITIZER FOR TUMOR TREATMENT

(75) Inventors: Nami Sugita, Ranzan (JP); Kenichi Kawabata, Kodaira (JP); Shinichiro Umemura, Hachioji (JP); Kazuaki Sasaki, Kokubunji (JP); Isao Sakata, Okayama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/801,844

(22) Filed: Mar. 9, 2001

(65) Prior Publication Data

US 2001/0041163 A1 Nov. 15, 2001

(30) Foreign Application Priority Data

Mar. 9, 2000 (JP) ........................................ 2000-070978

(51) Int. Cl.[7] ........................... A61B 8/00; C07D 311/82
(52) U.S. Cl. ........................................ 424/9.5; 549/223
(58) Field of Search ........................... 424/9.5; 549/223

(56) References Cited

U.S. PATENT DOCUMENTS 4,924,009 A * 5/1990 Neckers et al. .............. 549/223
6,083,524 A * 7/2000 Sawhney et al. ........... 424/426
6,143,492 A * 11/2000 Makings et al.

OTHER PUBLICATIONS

Lamberts et al. "Rose Bengal and Non–Polar Derivatives: The Birth of Dye Sensitizers for Photooxidation". Tetrahedron (1985), 41(11),2183–90.*

* cited by examiner

Primary Examiner—Sreeni Padmanabhan
Assistant Examiner—Lauren Q. Wells
(74) Attorney, Agent, or Firm—Antonelli, Terry, Stout & Kraus, LLP

(57) ABSTRACT

A sensitizer for tumor treatment has a structure such that a lipophilic group and a hydrophilic group are bound to one and the same carbon atom in a compound containing a xanthene dye structure. It is important that the lipophilic group and hydrophilic group are bound to one and the same carbon atom; if they are separated from each other, no sufficient effect is obtained. Thus, the sensitizer possesses both lipophilicity and hydrophilicity. This sensitizer has a function of promoting acoustic cavitation and a function of revealing an antitumor effect and is an agent highly accumulable in tumor tissues. Thus, this sensitizer is highly selective for tumor tissues and enables the treatment of malignant tumor using ultrasound.

8 Claims, 11 Drawing Sheets

SENSITIZER FOR TUMOR TREATMENT

BACKGROUND OF THE INVENTION

The present invention relates to a sensitizer for tumor treatment, which is to be used in the treatment of such a disease as tumor by ultrasound irradiation, and to an ultrasonic treatment system and a modality of ultrasonic therapy, in which that sensitizer is used. More specifically, it relates to a sensitizer given the amphiphilicity (both hydrophilicity and lipophilicity) and thus increased in its accumulation in the tumor tissue as derived from a sensitizer having a xanthene dye structure by modifying that structure, and to an ultrasonic treatment system and a modality of ultrasonic therapy, in which that sensitizer is used.

In recent years, even in cancer treatment, attention has been paid to the quality of life of posttreatment patients and, therefore, treatment modalities by which the region of tumor alone might be treated selectively and which would cause less damage to the body except for the region of tumor have been demanded. To develop such a modality of therapy, sonodynamic therapy which uses ultrasound and a sensitizer therefor (Reference 1: Jpn. J. Cancer Res., 80, 219–222, 1989) has become a target of study.

In this modality, an agent administered in advance is activated locally as an antitumor agent by means of waves and thereby the tumor region alone is treated, like in photodynamic therapy (Reference 2: Cancer Res., 39, 146–151, 1979) which is already in clinical application.

In photodynamic therapy, there is a theoretical problem that since the wavelength of a laser beam, thereof the attenuation coefficient in the living body, is restricted, the target of treatment is limited to superficial tumor located at most several millimeters deep from the surface. On the other hand, in sonodynamic therapy, the relation between the wavelength of an ultrasonic wave and the attenuation coefficient thereof is appropriate to the human body and therefore the therapy is characterized in that ultrasonic waves can be focused not only on superficial tumor but also on tumor located in a deep region. Therefore, sonodynamic therapy, if put to practical use, is expected to play a role in low invasive therapy, along with photodynamic therapy, in the target of therapy where it is preferable.

Referring to the above-mentioned sonodynamic therapy, various techniques have been explored through physical and chemical approaches and new techniques have been developed with respect to both system and agent.

In sonodynamic therapy, acoustic cavitation is thought to play an important role in the mechanisms of that therapy. Acoustic cavitation is a phenomenon of bubbles formed upon ultrasound irradiation growing and collapsing, and biological reactions are produced mechanically and chemically by the very high pressure and temperature temporarily generated on the occasion of the collapse.

Techniques for efficiently introducing this acoustic cavitation have been developed, for example the technique comprising irradiating ultrasound while switching the acoustic fields (Reference 3: JP Kokai H02-126848) and the technique comprising superimposing the second harmonics on the fundamentals (Reference 4: International laid-open Patent Specification WO 94/06380). When these techniques are used, acoustic cavitation can be introduced at a lower level of acoustic intensity.

On the other hand, through the agent side approach, the present inventors previously proposed an acoustic cavitation promoter for lowering the acoustic intensity threshold required for introducing acoustic cavitation in which a sensitizer having a xanthene dye structure is used (Reference 5: International laid-open Patent Specification WO 98/01131).

Further, it is known, as a basic mechanism of sonodynamic tumor treatment, that the use of a substance capable of generating active oxygen due to a chemical effect of ultrasound can increase the sonochemical antitumor effect (Reference 6: JP Kokai H06-29196). It is also known that sensitizers having a xanthene dye structure, which are acoustic cavitation promoters, are active oxygen-producing substances.

BRIEF SUMMARY OF THE INVENTION

In addition to the foregoing, it is important that the agent be capable of being accumulated in tumor tissues. In sonodynamic therapy, the spatial selectivity of the region to be treated is attained principally by the irradiation of focused ultrasound. However, when the treatment of that tumor located in a deep region of a living body or the treatment of a tumor species showing a complicated boundary between normal tissues and tumor tissues, such as infiltrative or disseminated tumor, is taken into consideration, it is essential for realizing safer and more effective therapy that the agent to be administered be itself capable of being accumulated in tumor tissues.

Therefore, for an agent to be ideal for sonodynamic therapy, it is desired that the agent have three characteristics simultaneously, namely (1) acoustic cavitation promoting activity, (2) ability to produce antitumor effects and (3) potential for being accumulated in tumor tissues.

Tumor tissues tend to take up lipoproteins to maintain their vigorous growth and have lymphoid tissues poorly formed, hence lipoproteins once taken up by them can hardly be excreted therefrom. A highly lipophilic agent, which has high affinity for lipoproteins, is thought to migrate with lipoproteins and be readily accumulated in tumor tissues. On the other hand, for an agent to be administered to the living body, it is essential that the agent have hydrophilicity as well.

Therefore, for an agent to be capable of being accumulated in tumor cells, it is desirable that the agent be endowed with a balance between lipophilicity and hydrophilicity and be high in both characteristics, namely be amphiphilic. Sensitizers having a xanthene dye structure are generally very high in hydrophilicity but very low in lipophilicity and, therefore, for improving their accumulation in tumor tissues, it is conceivable that their lipophilicity be increased. For increasing the lipophilicity, it is a common practice to introduce a lipophilic functional group such as an alkyl group. With such type of compound, however, the hydrophilic region is remote from the lipophilic region in the molecule, hence the compound will supposedly take a micelle-like form in body fluids; the possibility that the above characteristics (1) and (2) originally possessed by the compound be adversely affected is high.

Accordingly, it is an object of the present invention to provide a sensitizer containing a xanthene dye structure and endowed with the characteristic (3), namely ability to be accumulated in tumor tissues, without the above characteristics (1) and (2) being impaired.

One of the approaches for obtaining the compound aimed at by the invention is the one previously proposed by the present inventors and described in the above-cited reference 5. This comprises dimerizing a sensitizer having a xanthene dye structure and serving as an acoustic cavitation promoter simultaneously having antitumor activity to thereby render the same lipophilic.

Since, however, such sensitizer dimerization has problems on synthesizes, for example a lot of labor is required for isolation, the inventors made attempts to obtain a desired compound through another approach. The process in which the present invention was created is described below in detail.

When an attempt is made to improve the lipophilicity of an agent by mere introduction of a lipophilic group, in particular when a lipophilic group is introduced while sacrificing a hydrophilic functional group, the hydrophilicity may possibly decrease and the administration to a living body may become difficult. It is conceivable that a hydrophilic group be newly introduced to avoid the decrease in hydrophilicity due to lipophilic group introduction. However, in such a case, too, if the lipophilic group and hydrophilic group introduced are intramolecularly remote from each other, the product agent will become micelle-like in body fluids, as discussed above, and the cavitation promoting effect will expectedly decrease due to such change in characteristics.

From such viewpoint, the inventors made investigations concerning derivatives having a lipophilic group (R1) and a hydrophilic group (R2) introduced on the same carbon atom, as shown below by Formula 1, as candidate sensitizers containing a xanthene dye structure.

FORMULA 1

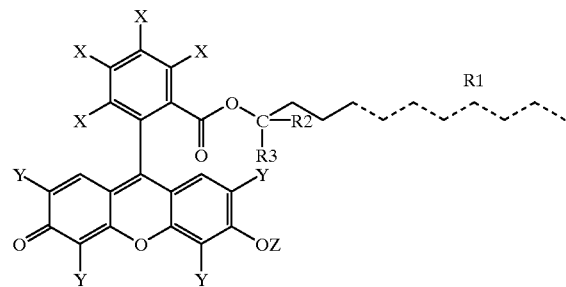

In Formula 1, X and Y each is a halogen atom or a hydrogen atom, Z is an alkali metal atom, such as Na or K, or a hydrogen atom, R1 is a lipophilic group, R2 is a hydrophilic group and R3 may be a lipophilic group R1 or a hydrophilic group R2 or a hydrogen atom.

During the investigations, it was revealed that, for the effect of the hydrophilic group R2 to be produced to the full, it is important to employ, as the lipophilic group R1, a straight chain alkyl group, for instance, which can take various three-dimensional configurations according to the milieu (e.g. solvent).

The number of carbon atoms contained in the straight chain alkyl group is desirably 3 to 30 and the optimal number of carbon atoms may vary depending on the level of hydrophilicity of the hydrophilic group R2 and/or the structure of the lipophilic group R1.

It was further found that when an alkyl group having a side chain or chains is employed in lieu of such straight chain alkyl group to serve as the lipophilic group R1, the same effect can be produced. Further, it was found that a functional group derived from a straight or side-chain-containing alkyl group by substitution of a double bond and/or a triple bond for part of the single bonds (C—C) thereof, a functional group derived from a straight or side-chain-containing alkyl group by substitution of an aromatic ring (for example benzene ring), or a functional group derived from a straight or side-chain-containing alkyl group by partial introduction of an ether linkage, ester linkage, amido group, sulfur atom or the like is also effective in producing the same effect. Specific examples of the lipophilic group R1 are shown in Table 1. They are by no means limitative of the scope of the invention, however.

In Table 1, there are shown straight alkyl groups, side-chain-containing alkyl groups, functional groups derived from a straight alkyl group by substitution of a double bond for part of the single bonds (C—C) thereof, functional groups derived from a straight alkyl group by substitution of a triple bond for part of the single bonds (C—C) thereof, functional groups resulting from the binding of a phenyl group to the terminus of a straight alkyl group, functional groups resulting from the binding of phenyl isothiocyanate to the terminus of a straight alkyl group, functional groups resulting from the binding of phenylsulfonyl chloride to the terminus of a straight alkyl group, straight chain ether, straight chain ester and straight chain amido groups. The use of one of these is preferred in the practice of the present invention.

TABLE 1

| | |
|---|---|
| Straight-chain alkyl group | 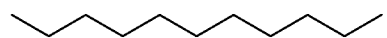 |
| Example of alkyl group with side chain | 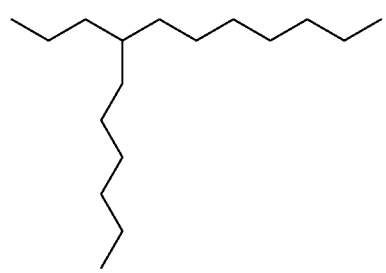 |
| Example including double bond | 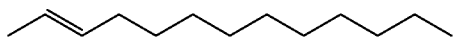 |

TABLE 1-continued

| | |
|---|---|
| Example including triple bond | 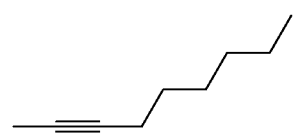 |
| Example including ether linkage | 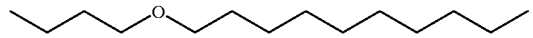 |
| Example including ester linkage | 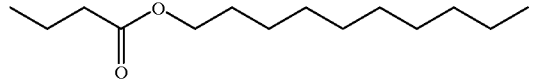 |
| Example including amido group | 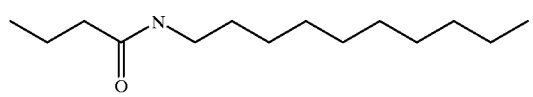 |
| Example including benzene ring | 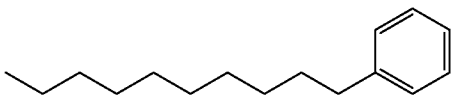 |
| Example including phenyl isothiocyanate | 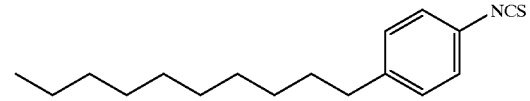 |
| Example including phenylsulfonyl chloride | 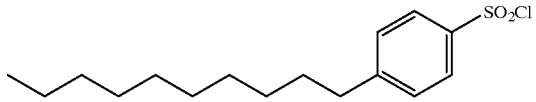 |

Desirable as the compound to be used in the practice of the invention are sensitizers containing a xanthene dye structure such as those having the structure represented by Formula 1, for example rose bengal (x=Cl, Y=I), phloxine B (X=Cl, Y=Br), 3,4,5,6-tetrachlorofluorescein (X=Cl, Y=H), erythrosine B (X=H, Y=I), and the sodium salt of each of them.

It is known that when sensitizers having such a xanthene dye structure have intramolecularly a halogen atom or a functional group capable of chemically binding to a thiol group or amino group included in proteins in the cell membrane, an improvement in their effect can result. In the practice of the present invention as well, the effect can be increased by employing such a structure.

It is desirable that the halogen comprise at least one of fluorine (F), chlorine (Cl), bromine (Br) and iodine (I). It is particularly desirable that one of X and Y in Formula 1 be a halogen.

The functional group capable of binding to proteins desirably comprises at least one of aziridine, amido, isothiocyanate, imido and sulfonyl chloride groups. In Formula 1, the carbon atom (C) to which the lipophilic group R1 and hydrophilic group R2 are bound is bonded to a sensitizer having a xanthene dye structure via ester bonding. It is to be understood that the scope of the invention is not limited by such mode of binding. In the case of compounds having such a structure, however, the introduction by ester bonding is the most expedient.

As a method of obtaining compounds to be used in the practice of the invention, a method is shown below for synthesizing compounds by introducing a straight alkyl group as lipophilic group R1 and a carboxyl group as hydrophilic group R2 into a sensitizer having a xanthene dye structure (such compounds, namely -α-carboxyalkyl esters, are hereinafter referred to as —COOH—Cn, n being the number of carbon atoms contained in the straight alkyl group). The method is by no means limitative of the scope of the invention, however.

These compounds can be synthesized according to the route shown in Equation 1 with reference to Reference 7 (Z. Naturforsch., B; Anorg. Chem. Org. Chem., 39B, 474–484, 1984) and the desired compounds containing a xanthene dye structure as represented by Formula 4 are obtained.

EQUATION 1

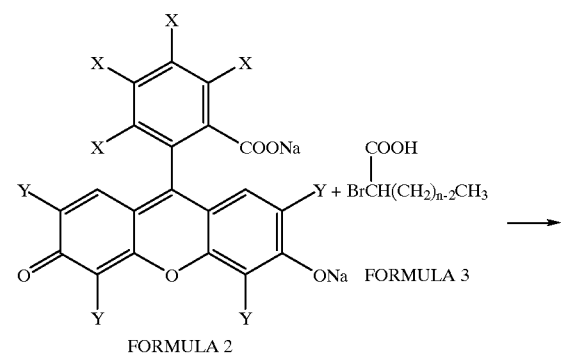

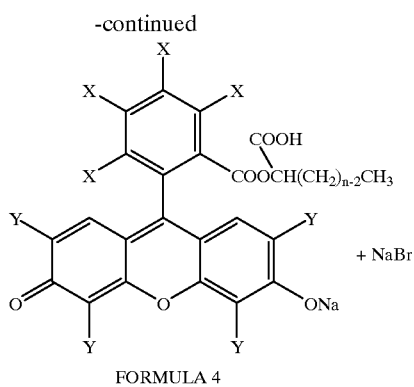

FORMULA 4

In Equation 1, X and Y are as defined above referring to Formula 1 and n represents the number of carbon atoms in the alkyl group and desirably n=3 to 20.

This reaction is the so-called nucleophilic replacement reaction between the carboxylate part (COO) of the sensitizer having a xanthene dye structure as represented by Formula 2 and the halogenide of a fatty acid as represented by Formula 3. The particulars of this synthesis are described later in Example 1.

Variations of the number of carbon atoms in the lipophilic alkyl group shown in Formula 4 can be obtained by submitting fatty acid halogenides differing in the number of carbon atoms to the reaction. The halogenides of this kind are commercially available.

The above halogenides can also be synthesized from a fatty acid having the desired number of carbon atoms by bromination of the a position thereof using phosphorus trichloride as a catalyst as described in Reference 8 (Org. Synth., I, 115–116, 1941).

In the practice of the invention, the hydrophilic group R2 desirably comprises at least one of a carboxy group or its soluble salt, a sulfonic acid group or its soluble salt, a sulfuric acid ester group or its soluble salt, a hydroxy group or its soluble salt, an amine group or its soluble salt, a quaternary ammonium group or its soluble salt and a phosphoric acid group or its soluble salt.

In some instances, the group R2 may contain lipophilic structures such as alkyl group, ether linkage, amido group, ester linkage or benzene ring or a like. For example, it is known that an ether linkage has low hydrophilicity itself, but an ether linkage can form polyethylene glycol resulting from the combination of a plurality of ether bonds, alkyl groups and hydroxy groups, thereby polyethylene glycol shows high hydrophilicity. Examples of the functional groups or soluble salts mentioned above as well as examples of the combinations thereof are shown in Table 2, without any meaning restrictive of the scope of the invention.

TABLE 2

| | |
|---|---|
| Carboxy group and its salt | —COOH, —COO$^-$Na$^+$ |
| Sulfonic acid group and its salt | —SO$_3$H, —SO$_3^-$Na$^+$ |
| Sulfuric ester group and its salt | —OSO$_3$H, —OSO$_3^-$Na$^+$ |
| Hydroxy group and its salt | —OH, —O$^-$Na$^+$ |
| Amine group and its salt | —NH$_2$, —N$^+$H$_2$RCl$^-$ |
| Quaternary ammonium group and its salts | —NR$_4$, —N$^+$R$_3$Cl$^-$ |
| Phosphoric acid group and its salt | —OPO(OH)$_2$, —OPO(ONa)$_2$ |
| Polyethylene glycol | —(OCH$_2$CH$_2$)$_n$OH |
| Example including amido group | —CON(OCH$_2$CH$_2$)$_n$OH |
| Example including ester linkage | —CO(OCH$_2$CH$_2$)$_n$OH |

In Table 2, R represents a functional group such as a chain-like alkyl group, and a cyclic N compound such as a pyridinium salt is preferred as the quaternary ammonium salt. As for n, it is preferred that n=3 to 20.

While Equation 1 illustrate a synthetic pathway for —COOH—Cn compounds in which the hydrophilic group R2 is a carboxy group, compounds having another hydrophilic group introduced can be synthesized in the same manner using a halogenide having the respective hydrophilic group.

For example, the halogenide of a compound in which the hydrophilic group is a sulfonate can be synthesized by the method described in Reference 9 (J. Am. Chem. Soc., 62, 1044, 1940). This synthetic pathway is illustrated by Equation 2 and Equation 3.

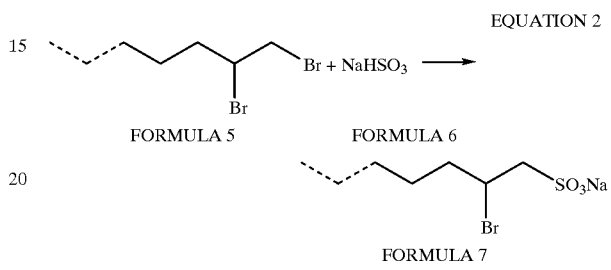

EQUATION 2

FORMULA 5    FORMULA 6

FORMULA 7

EQUATION 3

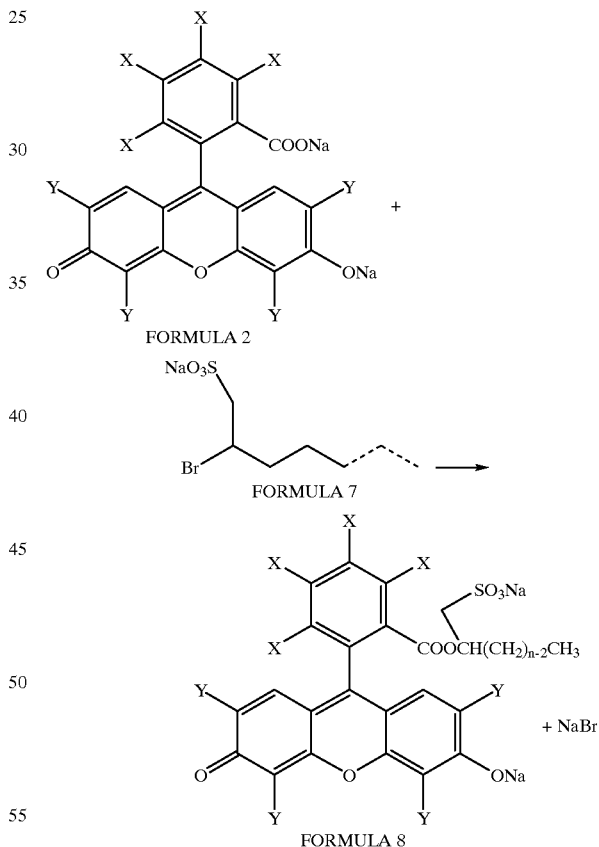

FORMULA 2

FORMULA 7

FORMULA 8

In Equation 3, X and Y are as defined above referring to Formula 1 and n represents the number of carbon atoms in the alkyl group and preferably n=10 to 30.

First, an unsymmetrically dihalogenated alkane (Formula 5) is sulfonated using a sulfite (Formula 6). The sulfonated compound (Formula 7) obtained is reacted with a xanthene dye, whereby the desired sulfonated compound containing a xanthene dye structure as represented by Formula 8 is obtained. The particulars of this synthesis are shown later in Example 2.

Compounds in which the hydrophilic group R2 is a carboxylate can be prepared from —COOH—Cn by converting the carboxylic acid to the carboxylate (this method is mentioned in detail in Example 3).

To sum up, the sensitizer for sonodynamic therapy according to the invention which contains a xanthene dye structure is characterized by its structure such that at least one hydrophilic group R2 and at least one lipophilic group R1 are always bound to one and the same carbon atom. This lipophilic group R1 desirably comprises a straight alkyl group containing 3 to 30 carbon atoms, and the alkyl group may partly contain at least one of a branched alkyl group, double bond, triple bond, aromatic ring (e.g. benzene ring), ether linkage, ester linkage, amido group, sulfur, etc.

The hydrophilic group R2 desirably comprises at least one of a carboxy group or its soluble salt, a sulfonic acid group or its soluble salt, a sulfuric acid ester group or its soluble salt, a hydroxy group or its soluble salt, an amine group or its soluble salt, a quaternary ammonium group or its soluble salt and a phosphoric acid group or its soluble salt.

The ultrasonic treatment system according to the invention comprises a transducer for targeting, an ultrasonic therapeutic transducer, a controller and an acoustic-cavitation monitor for detecting the acoustic cavitation induced by the sensitizer of the invention and adequately maintaining the site and intensity of ultrasound irradiation, among others.

The acoustic cavitation detecting means is not restricted but may be any means capable of measuring a physical phenomenon caused by acoustic cavitation. Thus, means for measuring such an acoustic phenomenon as a subharmonic or harmonic waves or means for measuring light emission may be used.

In the following, the constitution of the present invention is described.

The sensitizer (A) for tumor treatment according to the invention is characterized in that it has the skeleton of xanthene dyes and has a structure such that at least one hydrophilic group and at least one lipophilic group are bound to one and the same carbon atom occurring in a functional group bound to a carbon atom in that skeleton. It is a sensitizer for tumor treatment which can enhance the effect of tumor treatment as produced by ultrasound irradiation.

The sensitizer for tumor treatment according to the invention has a functional group capable of chemically binding to the thiol or amino group and the functional group comprises at least one of aziridine, amido, isothiocyanate, imido and sulfonyl chloride groups.

More specifically, the sensitizer (B) for tumor treatment according to the invention is characterized in that it has the skeleton of xanthene dyes and has a structure such that at least one hydrophilic group and at least one lipophilic group are bound to one and the same carbon atom occurring in a functional group bound to a carbon atom in that skeleton and that it has the structure represented by Formula 1. In Formula 1, X and Y each is a halogen atom or a hydrogen atom, Z is an alkali metal atom or a hydrogen atom, R1 is a lipophilic group, R2 is a hydrophilic group and R3 is a hydrophilic group R1 or a hydrophilic group R2 or a hydrogen atom. Typical examples of this sensitizer for tumor treatment are described in the following.

X and Y each is a halogen atom and Z is an alkali metal atom.

The lipophilic group R1 is a lipophilic group comprising a straight alkyl group containing 3 to 30 carbon atoms.

The lipophilic group R1 is one of straight alkyl groups, side-chain-containing alkyl groups, functional groups derived from a straight or side-chain-containing alkyl group by substitution of a double bond for part of the single bonds thereof, functional groups derived from a straight or side-chain-containing alkyl group by substitution of a triple bond for part of the single bonds thereof, functional groups derived from a straight or side-chain-containing alkyl group by the binding of an aromatic ring thereto, and functional groups derived from a straight or side-chain-containing alkyl group by partial introduction of at least one of an ether linkage, an ester linkage, an amido group and a sulfur atom.

The hydrophilic group R2 is a hydrophilic group comprising at least one of a carboxy group or its soluble salt, a sulfonic acid group or its soluble salt, a sulfuric acid ester group or its soluble salt, a hydroxy group or its soluble salt, an amine group or its soluble salt, a quaternary ammonium group or its soluble salt and a phosphoric acid group or its soluble salt.

The ultrasonic treatment system according to the invention comprises an ultrasonic imaging probe for irradiating a target for treatment in a living body with ultrasound for imaging to thereby obtain a diagnostic ultrasonic image of the target for treatment, an ultrasonic therapeutic transducer for irradiating the target for treatment with ultrasound for treatment, a controller for adjusting the intensity and/or focus of the ultrasound for treatment based on the diagnostic ultrasonic image, an ultrasonic transducer for generating bubbles which generates ultrasound for irradiating the target for treatment with administered sensitizer (A) for tumor treatment illustrated hereinabove and generates bubbles, which are stabilized by the sensitizer for tumor treatment, by irradiation with the ultrasound, and a display device for displaying the diagnostic ultrasonic image obtained by the ultrasonic imaging probe and contrasted by the bubbles. After the diagnostic ultrasonic image as contrasted by the bubbles is displayed on the display device, the ultrasound for treatment is irradiated on the target for treatment.

In another aspect, the ultrasonic treatment system according to the invention comprises an ultrasonic imaging probe for irradiating a target for treatment in a living body with ultrasound for imaging to thereby obtain a diagnostic ultrasonic image of the target for treatment, an ultrasonic therapeutic transducer for irradiating the target for treatment with ultrasound for treatment, a controller for adjusting the intensity and/or focus of the ultrasound for treatment based on the diagnostic ultrasonic image, an ultrasonic transducer for generating bubbles which generates ultrasound for irradiating the target for treatment with administered sensitizer (B) for tumor treatment illustrated hereinabove and generates bubbles, which are stabilized by the sensitizer for tumor treatment, by irradiation with the ultrasound, and a display device for displaying the diagnostic ultrasonic image obtained by the ultrasonic imaging probe and contrasted by the bubbles. After the diagnostic ultrasonic image as contrasted by the bubbles is displayed on the display device, the ultrasound for treatment is irradiated on the target for treatment.

The modality of ultrasonic therapy according to the present invention comprises (1) the step of irradiating a target for treatment in a living body with the ultrasound for imaging as generated from an ultrasonic imaging probe to thereby obtain a diagnostic ultrasonic image of the target for treatment, (2) the step of adjusting the intensity and/or focus of the ultrasound for treatment as generated from an ultrasonic therapeutic transducer based on the diagnostic ultrasonic image, (3) the step of irradiating the target for treatment with administered sensitizer (A) for tumor treatment illustrated hereinabove with the ultrasound generated by an ultrasonic transducer for generating bubbles to thereby generate bubbles, which are stabilized by the sensitizer for tumor treatment, by ultrasound irradiation, (4) the step of displaying the diagnostic ultrasonic image obtained by the ultrasonic imaging probe and contrasted by the bubbles and (5) the step of irradiating the target for treatment with the ultrasound for treatment after displaying of the diagnostic ultrasonic image as contrasted by the bubbles.

In another aspect, the modality of ultrasonic therapy according to the invention comprises (1) the step of irradiating a target for treatment in a living body with the ultrasound for imaging as generated from an ultrasonic imaging probe to thereby obtain a diagnostic ultrasonic image of the target for treatment, (2) the step of adjusting the intensity and/or focus of the ultrasound for treatment as generated from an ultrasonic therapeutic transducer based on the diagnostic ultrasonic image, (3) the step of irradiating the target for treatment with administered sensitizer (B) for tumor treatment illustrated hereinabove with the ultrasound generated by an ultrasonic transducer for generating bubbles to thereby generate bubbles, which are stabilized by the sensitizer for tumor treatment, by ultrasound irradiation, (4) the step of displaying the diagnostic ultrasonic image obtained by the ultrasonic imaging probe and contrasted by the bubbles and (5) the step of irradiating the target for treatment with the ultrasound for treatment after displaying of the diagnostic ultrasonic image as contrasted by the bubbles.

The sensitizer for ultrasonic therapy according to the invention possesses both lipophilicity and hydrophilicity. It is important that the lipophilic group and hydrophilic group are bound to one and the same carbon atom in the molecule. When they are remote from each other, no sufficient effect is obtained. The sensitizer of the invention is an agent having the function of inducing acoustic cavitation and the function of revealing an antitumor effect and capable of being highly accumulated in tumor tissues. Namely, the sensitizer of the invention is high in selectivity for tumors and can enhance the effect of tumor treatment, thus enabling the treatment of malignant tumor with ultrasound.

DETAILED DESCRIPTION OF THE INVENTION

Figure 1:
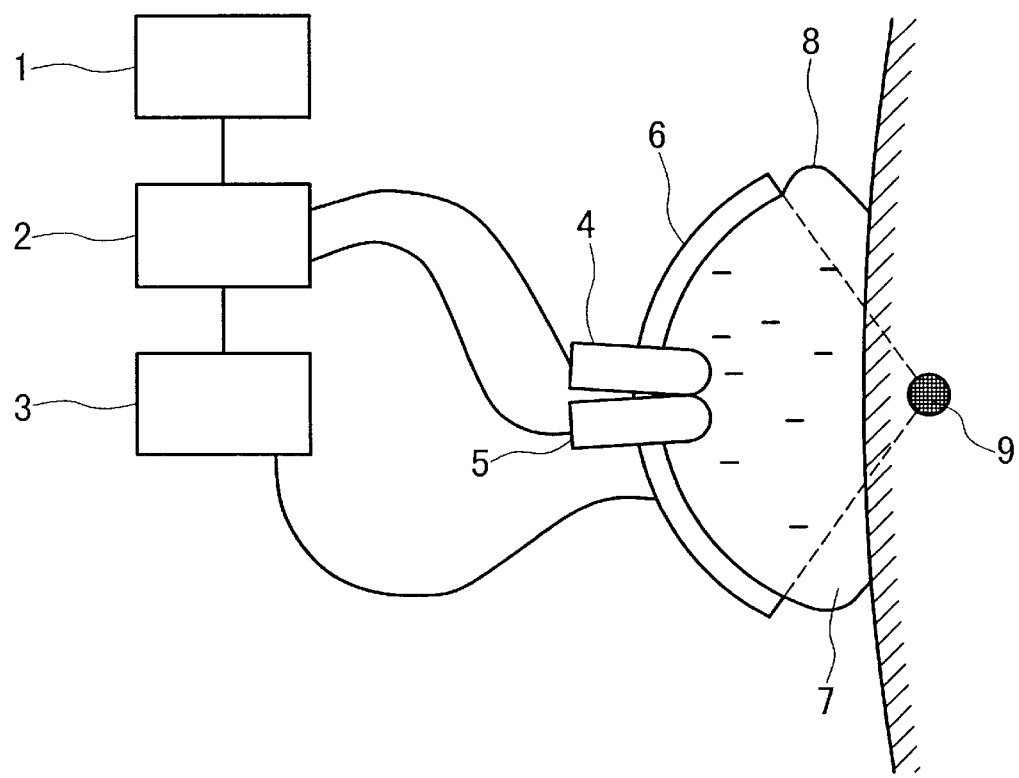
FIG. 1 is a schematic representation of the ultrasonic treatment system according to an example of the invention.

As explained hereinabove, the sensitizer for tumor treatment containing a xanthene dye structure according to the invention, possesses both lipophilicity and hydrophilicity and has excellent characteristics as a sensitizer which accumulates in tumor tissues.

The sensitizer of the invention shows increased accumulation in tumor tissues as the result of its having a structure such that at least one hydrophilic group and at least one lipophilic group are bound to one and the same carbon atom. At the same time, the sensitizer has a surfactant-like property owing to the balance between the hydrophilic group and lipophilic group. Owing to this property, it shows a high bubble stabilizing effect as well. Owing to this effect, it has good characteristics also as an ultrasonic contrast agent for use in combination with means for generating bubbles.

In particular, the sensitizer of the invention has an effect of promoting acoustic cavitation upon ultrasound irradiation, as shown in Test Examples 5, 6 and 7, and, since this acoustic cavitation accompanies bubble generation, ultrasound irradiation can be used as means for generating bubbles.

The following synthesis examples for those sensitizers of the invention which accumulate in tumor tissues and the following test examples demonstrating the effectiveness thereof illustrate the present invention in further detail. These examples are, however, by no means limitative of the scope of the invention.

Example 1

This example is a synthesis example for the xanthene-dye-structure-containing sensitizer-α-carboxyalkyl esters (—COOH—Cn) (n being the number of carbon atoms in the straight chain alkyl group) of the invention.

(1) Rose bengal-α-carboxyheptyl ester (RB—COOH—C7)

A round-bottom flask equipped with a stirring bar and a condenser was charged with 1.0 g (0.9 mmol) of rose bengal sodium salt (hereinafter referred to as RB for short) and 10 mL (milliliters) of N,N-dimethylformamide (hereinafter referred to as DMF for short) and the contents were stirred until dissolution of RB.

To this reddish pink solution was added 1.3 g (6.0 mmol) of 2-bromooctanoic acid and the mixture was heated at 70° C. (outside temperature) with stirring for 6 hours. The progress of the reaction was monitored by thin layer chromatography (developing solvent: ethyl acetate:benzene:acetic acid=76:19:6 by weight) and, after confirmation of the disappearance of the raw material, the reaction procedure was finished.

The DMF was removed from the substance at the end of the reaction at about 70° C. under reduced pressure, the residue was cooled to room temperature, diethyl ether was added and the mixture was stirred overnight. The mixture was then filtered under reduced pressure, and the solid thus obtained was purified by column chromatography (stationary phase: silica gel, mobile phase: diethyl ether, acetone) to give 0.64 g (0.56 mmol) of the desired substance (RB—COOH—C7) as a purplish red powder (yield 62%).

RB—COOH—C7 was measured for $^1$H and $^{13}$C nuclear magnetic resonance (hereinafter referred to as NMR for short) spectra with dimethyl sulfoxide (hereinafter referred to as DMSO for short) —d6 as a solvent and as an internal standard. The measured chemical shift values (δ ppm) are shown below.

$^1$H NMR (δ ppm): 8.43 (br. s, —OH); 7.44, 7.43 (s, 1HX2, H-1, 8); 4.64 (dd, 1H, J=4.4 Hz, 7.2 Hz, —O—CH—); 1.35–1.25 (m, 2H, —CH$_2$—); 1.17 (m, 2H, J=7.4 Hz, —CH$_2$—); 1.09–0.97 (m, 4H, —CH$_2$—); 0.94–0.88 (m, 2H, —CH$_2$—); 0.81 (t, 3H, J=7.3 Hz, —CH$_3$)

$^{13}$C NMR (δ ppm): 171.8, 171.8 (C-3, 6); 169.4 (—COOH); 162.5 (—C=O—) 157.4, 157.2 (C-4a, 4b); 136.2, 135.9 (C-1, 8); 139.3, 135.2, 134.5, 132.9, 131.9, 130.2, 129.1 (C-1'~6', C-9); 110.9, 110.7 (C-8a, 8b); 97.3, 97.1 (C-4, 5); 76.0, 75.8 (C-2, 7); 74.0 (—OCH—); 30.8, 30.2, 28.1, 24.1, 22.1 (—CH$_2$—); 14.0 (—CH$_3$)

(2) Carboxylic acid derivatives of other xanthene dye type sensitizers:

The respective sodium salts were used as starting materials and the same procedure as mentioned above was followed to give the desired sensitizers. Some examples are shown below.

(a) Phloxine B-α-carboxyheptyl ester (PB—COOH—C7):

The same procedure as mentioned above under (1) was followed using 0.10 g (0.12 mmol) of phloxine B sodium salt (hereinafter, PB), 0.15 g (0.67 mmol) of 2-bromooctanoic acid and 2 mL of DMF. After allowing the reaction to proceed for 4 hours, 0.056 g (0.059 mmol) of the desired substance was obtained as a red powder (yield 49%). The chemical shift values (δ ppm) as measured by NMR are shown below.

$^1$H NMR (δ ppm): 8.30 (br. s, —OH); 7.32, 7.32 (s, 1HX2, H-1, 8); 4.69 (dd, 1H, J=4.2 Hz, 7.4 Hz, —O—CH—); 1.42–1.26 (m, 2H, —CH$_2$—); 1.17 (m, 2H, J=7.1 Hz, —CH$_2$—); 1.11–0.99 (m, 4H, —CH$_2$—); 0.98–0.92 (m, 2H, —CH$_2$—); 0.81 (t, 3H, J=7.0 Hz, —CH$_3$)

$^{13}$C NMR (δ ppm): 169.3 (—COOH); 168.7, 168.6 (C-3, 6); 162.5 (—C=O—); 153.1, 153.0 (C-4a, 4b); 141.3, 135.2, 134.5, 132.8, 131.9, 130.1, 129.1 (C-1'~16', C-9); 129.2, 128.8 (C-1, 8); 119.3, 119.2 (C-8a, 8b); 109.3, 109.0 (C-4, 5); 99.5, 99.3 (C-2, 7); 73.9 (—O—CH—); 30.8, 30.1, 28.0, 23.9, 21.9 (—CH$_2$—); 13.8 (—CH$_3$)

(b) Erythrosine B-α-carboxyheptyl ester (EB—COOH—C7):

The same procedure as mentioned above under (1) was followed using 0.11 g (0.13 mmol) of erythrosine B sodium salt (hereinafter, EB), 0.19 g (0.85 mmol) of 2-bromooctanoic acid and 2 mL of DMF. After allowing the reaction to proceed for 7 hours, 0.066 g (0.066 mmol) of the desired substance was obtained as a red powder (yield 51%). The chemical shift values (δ ppm) as measured by NMR are shown below.

$^1$H NMR (δ ppm): 8.43 (br. s, —OH); 8.12–8.09 (m, 1H, Ph); 7.57–7.50 (m, 2H, Ph); 7.23 (s, 2H, H-1, 8); 7.15–7.14 (m, 1H, Ph); 4.64 (dd, 1H, J=4.4 Hz, 7.2 Hz, —O—CH—); 1.41–1.23 (m, 4H, —CH$_2$—); 1.01–0.77 (m, 6H, —CH$_2$—); 0.64 (t, 3H, J=7.0 Hz, —CH$_3$)

$^{13}$C NMR (δ ppm): 171.2, 171.2 (C-3, 6); 169.4 (—COOH); 162.5 (—C=O—); 157.4, 157.2 (C-4a, 4b); 137.4, 137.1 (C-1, 8); 139.3, 135.2, 134.5, 132.9, 131.9, 130.2, 129.1 (C-1'~16', C-9); 111.7, 111.5 (C-8a, 8b); 95.2, 95.9 (C-4, 5); 74.9, 74.7 (C-2, 7); 74.0 (—O—CH—); 30.9, 30.3, 28.3, 24.6, 22.1 (—CH$_2$—); 13.9 (—CH$_3$)

(3) Compounds differing in the number of carbon atoms in the alkyl group:

Using bromides of fatty acids differing in the number of carbon atoms, the same procedure as mentioned above was followed to give the desired sensitizers. Several examples are shown below.

(c) Rose bengal-α-carboxyethyl ester (RB—COOH—C2):

The same procedure as mentioned above under (1) was followed using 1.01 g (0.99 mmol) of RB, 0.45 mL (5.0 mmol) of 2-bromopropionic acid and 10 mL of DMF. After allowing the reaction to proceed for 4 hours, 0.71 g (0.67 mmol) of the desired substance was obtained as a purplish red powder (yield 68%). The chemical shift values (δ ppm) as measured by NMR are shown below.

$^1$H NMR (δ ppm): 8.24 (br. s, —OH); 7.44 (br. s, 2H, H-1, 8); 4.76 (q, 1H, J=6.8 Hz, —O—CH—); 0.96 (d, 3H, J=7.0 Hz, —CH$_3$)

$^{13}$C NMR (δ ppm): 172.1, 172.0 (C-3, 6); 170.2 (—COOH); 162.4 (—C=O—); 157.6, 157.4 (C-4a, 4b); 136.5, 136.2 (C-1, 8); 139.5, 135.4, 134.7, 133.0, 132.1, 130.4, 129.2 (C-1'~6', C-9); 111.3, 110.9 (C-8a, 8b); 97.2, 97.1 (C-4, 5); 75.9, 75.8 (C-2, 7); 70.5 (—O—CH—); 16.1 (—CH$_3$)

(d) Rose bengal-a-carboxybutyl ester (RB—COOH—C4):

The same procedure as mentioned above under (1) was followed using 1.01 g (0.99 mmol) of RB, 0.92 g (5.1 mmol) of 2-bromopentanoic acid and 10 mL of DMF. After allowing the reaction to proceed for 8 hours, 0.32 g (0.30 mmol) of the desired substance was obtained as a purplish red powder (yield 30%). The chemical shift values (δ ppm) as measured by NMR are shown below.

$^1$H NMR (δ ppm): 8.43 (br. s, —OH); 7.44, 7.43 (s, 1HX2, H-1, 8); 4.64 (dd, 1H, J=4.4 Hz, 7.2 Hz, —O—CH—); 1.35–1.25 (m, 2H, —CH$_2$—); 0.94–0.88 (m, 2H, —CH$_2$—); 0.81 (t, 3H, J=7.3 Hz, —CH$_3$)

$^{13}$C NMR (δ ppm): 171.8, 171.8 (C-3, 6); 169.4 (—COOH); 162.5 (—C=O—); 157.4, 157.3 (C-4a, 4b); 136.3, 135.9 (C-1, 8); 139.2, 135.2, 134.5, 132.9, 131.9, 130.2, 129.1 (C-1'~16', C-9); 111.0, 110.7 (C-8a, 8b); 97.2, 97.0 (C-4, 5); 75.9, 75.7 (C-2, 7); 73.8 (—O—CH—); 32.2, 17.6 (—CH$_2$—); 13.4 (—CH$_3$)

(e) Rose bengal-α-carboxypentadecyl ester (RB—COOH—C15):

The same procedure as mentioned above under (1) was followed using 1.00 g (0.98 mmol) of RB, 1.57 g (4.7 mmol) of 2-bromohexadecanoic acid and 10 mL of DMF. After allowing the reaction to proceed for 8 hours, 0.41 g (0.33 mmol) of the desired substance was obtained as a purplish red powder (yield 34%). The chemical shift values (δ ppm) as measured by NMR are shown below.

$^1$H NMR (δ ppm): 8.43 (br. s, —OH); 7.44, 7.43 (s, 1HX2, H-1, 8); 4.64 (dd, 1H, J=4.4 Hz, 7.2 Hz, —O—CH—); 1.44–1.34 (m, 2H, —CH$_2$—); 1.22 (br. s, 18H, —CH$_2$—); 1.09–0.97 (m, 4H, —CH$_2$—); 0.94–0.88 (m, 2H, —CH$_2$—); 0.81 (t, 3H, J=7.3 Hz, —CH$_3$)

$^{13}$C NMR (δ ppm): 171.7, 171.6 (C-3, 6); 169.4 (—COOH); 162.5 (—C=O—); 157.4, 157.2 (C-4a, 4b); 136.2, 135.8 (C-1, 8); 139.1, 135.1, 134.4, 133.0, 131.9, 130.2, 129.1 (C-1'~6', C-9); 110.8, 110.6 (C-8a, 8b); 97.1, 97.0 (C-4, 5); 75.9, 75.6 (C-2, 7); 74.1 (—O—CH—); 31.2, 30.1, 28.9, 28.8, 28.8, 28.6, 28.5, 28.3, 24.1, 22.0 (—CH$_2$—); 13.9 (—CH$_3$)

Example 2

Synthesis of sulfonate derivatives (—CH$_2$SO$_3$Na—Cn) (n being the number of carbon atoms in the straight chain alkyl group)

(a) Halogenated alkylsulfonate:

1,2-Dibromohexane (1.22 g, 5.0 mmol) was added to a solution of 0.6 g (5 mmol) of sodium sulfite in 20 mL of a 1:1 mixture of water and ethanol, and the resulting mixture was refluxed for 24 hours with vigorous stirring. The ethanol was then removed by distillation and the residual solution was allowed to stand at room temperature, whereupon white crystals precipitated. The crystals were filtered off under reduced pressure, washed with ether and dried to give 0.67 g (2.5 mmol) of the desired substance, namely sodium 2-bromohexylsulfonate (yield 50%).

(b) Rose bengal-α-sodium methylsulfonate-pentyl ester (RB—CH$_2$SO$_3$Na—C$_5$)

The same procedure as mentioned above under (1) was followed using 0.13 g (0.13 mmol) of RB, 0.035 g (0.13 mmol) of sodium 2-bromohexylsulfonate and 2 mL of DMF. After allowing the reaction to proceed for 7 hours, 0.084 g (0.071 mmol) of the desired substance was obtained as a red powder (yield 55%). The chemical shift values (δ ppm) as measured by NMR are shown below.

$^1$H NMR (δ ppm): 7.38, 7.37 (s, 1HX2, H-1, 8); 5.09 (m, 1H, —O—CH—) 3.60 (m, 2H, —CH$_2$—SO$_3$Na); 1.25–1.14 (m, 2H, —CH$_2$—) 1.09–0.97 (m, 2H, —CH$_2$—); 0.94–0.88 (m, 2H, —CH$_2$—) 0.81 (t, 3H, J=7.3 Hz, 1'CH$_3$)

$^{13}$C NMR (δ ppm): 171.7, 171.7 (C-3, 6); 162.6 (—C=O—); 157.4, 157.2 (C-4a, 4b); 136.1, 135.9 (C-1, 8); 139.3, 135.2, 134.5, 132.9, 131.9, 130.2, 129.1 (C-1'~6', C-9); 112.4 (—O—CH—); 111.2, 111.0 (C-8a, 8b); 97.1, 96.9 (C-4, 5); 76.0, 75.8 (C-2, 7); 54.4 (—CH$_2$—SO$_3$Na); 34.2, 32.2, 31.9, 22.7 (—CH$_2$—); 13.9 (—CH$_3$)

(c) Sulfonate derivatives of other xanthene dye sensitizers were obtained by the same procedure as mentioned above using the respective sodium salts as starting materials.

(d) Compounds differing in the number of carbon atoms in the alkyl group were obtained by the same procedure as mentioned above using halogenated alkylsulfonates differing in the number of carbon atoms.

Example 3

Synthesis of carboxylate derivatives (—COONa— Cn) (n being the number of carbon atoms in the straight chain alkyl group)

(a) Rose bengal-α-sodium carboxylate-heptyl ester (RB—COONa—C7):

A solution of 100 mg (0.088 mmol) of RB—COOH—C7 in 2 mL of DMF was added to a solution of 18 mg (0.45 mmol) of sodium hydroxide (NaOH) in 3 mL of methanol, and the mixture was stirred vigorously at room temperature for 3 days.

DMF (3 mL) was added, the methanol was removed by distillation under reduced pressure, the resulting white solid precipitate was removed by filtration under reduced pressure, the DMF was removed from the filtrate at about 70° C. under reduced pressure, the remaining filtrate was cooled to room temperature, diethyl ether was then added, and the mixture was stirred overnight.

Then, the mixture was filtered again under reduced pressure and the solid obtained was washed with two portions of diethyl ether to give 72 mg (0.062 mmol) of the desired substance (RB—COONa—C7) as a purplish red powder (yield 70%). The chemical shift values (δ ppm) as measured by NMR are shown below.

$^1$H NMR (δ ppm): 7.44, 7.43 (s, 1HX2, H-1, 8); 4.64 (dd, 1H, J=4.4 Hz, 7.2 Hz, —O—CH—); 1.35–1.25 (m, 2H, —CH$_2$—); 1.17 (m, 2H, J=7.4 Hz, —CH$_2$—); 1.09–0.97 (m, 4H, —CH$_2$—); 0.94–0.88 (m, 2H, —CH$_2$—); 0.81 (t, 3H, J=7.3 Hz, —CH$_3$)

$^{13}$C NMR (δ ppm): 175.0 (—COONa); 171.6, 171.6 (C-3, 6); 164.5 (—C=O—); 157.3, 157.0 (C-4a, 4b); 136.9, 136.8 (C-1, 8); 145.3, 143.3, 132.7, 130.4, 128.5, 127.5, 127.0 (C-1'~6', C-9); 112.0, 112.8 (C-8a, 8b); 98.3, 98.1 (C-4, 5); 77.6, 77.4 (C-2, 7); 74.0 (—O—CH—); 30.8, 30.2, 28.1, 24.1, 22.1 (—CH$_2$—); 14.0 (—CH$_3$)

(b) Carboxylate derivatives of other xanthene dye sensitizers were obtained by the same procedure as mentioned above using the respective —COOH—Cn species.

(c) Compounds differing in the number of carbon atoms in the alkyl group were obtained by the same procedure as mentioned above using —COOH—Cn species differing in the number of carbon atoms.

Example 4

This example illustrates an example of the ultrasonic treatment system in which the xanthene-dye-structure-containing sensitizer shown in each of the above examples is used as a sonochemical sensitizer.

Referring to FIG. 1, which is a schematic drawing showing the ultrasonic treatment system according to the invention, that system is described. The system is constituted of a monitor 1, a controller 2, a wave generator and amplifier 3, a transducer 4 for targeting, an acoustic-cavitation detector 5, an ultrasonic therapeutic transducer 6, and a matching layer 8 containing degassed water 7. And, it is constituted so that the focus of the ultrasonic therapeutic transducer 6 may be adjusted to the target 9 for treatment by means of the controller 2.

Further, it is constituted so that whether acoustic cavitation occurs at the desired site (target for treatment 9) or not can be detected by the acoustic-cavitation detector 5 and the intensity or focus of the therapeutic ultrasound can be changed by means of the controller 2.

The transducer 4 for targeting comprises a 3–10 MHz ultrasonic imaging probe. The acoustic-cavitation detector 5 comprises a hydrophone. The ultrasonic therapeutic transducer 6 is constituted so as to generate ultrasound using a piezoelectric device for a resonance frequency of 0.5 to 4.5 MHz.

In the following, some test examples illustrating the characteristics of the sonochemical sensitizer of the invention are described.

Test Example 1

Solubility measurement of RB and lipophilic derivatives of RB:

The sonochemical sensitizers of the invention, namely RB—COOH—Cn species (n being the number of carbon atoms in the straight alkyl group) were examined for their solubility in an aqueous solution and in an organic solvent. The aqueous solution used was a phosphate buffer solution (hereinafter, PBS) with a pH of 7.4 and the organic solvent used was 1-octanol.

First, saturated solutions of each RB—COOH—Cn in PBS and in 1-octanol were prepared at 25° C. and each solution was measured for its ultraviolet-visible absorption spectrum. Based on the molar absorptivity determined beforehand by measuring the ultraviolet-visible absorption spectrum of a solution having a known concentration, the agent concentration in the saturated solution was estimated.

For comparison, the starting material RB and two kinds of RB derivative, for which an attempt was made to increase the lipophilicity by a method other than that of the invention, namely rose bengal alkyl esters (hereinafter, RB—Cn, n being the number of carbon atoms in the alkyl group) and rose bengal fatty acid esters (hereinafter, RB—Cn—COOH, n being the number of carbon atoms in the methylene chain), were also subjected to solubility measurement.

The structural formulas of the respective compounds are represented by Formula 9, Formula 10, Formula 11 and Formula 12.

FORMULA 9

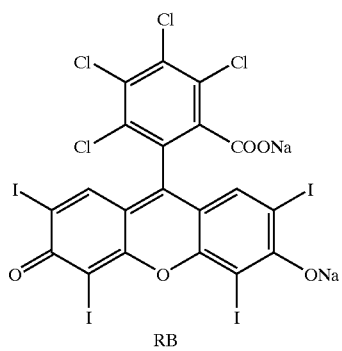

RB

FORMULA 10

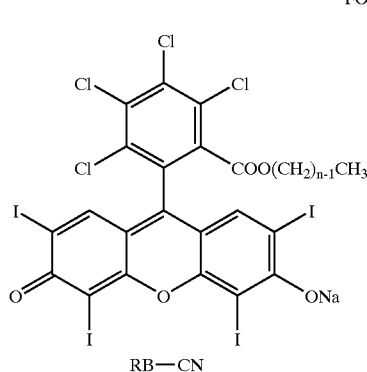

RB—CN

FORMULA 11

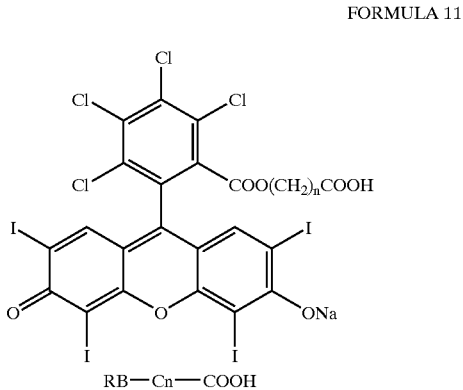

RB—Cn—COOH

FORMULA 12

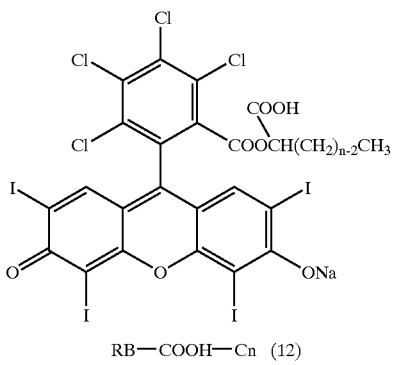

RB—COOH—Cn (12)

The RB—Cn species (Cn being $(CH_2)_{n-1}CH_3$ and n being the number of carbon atoms contained in the alkyl group) represented by Formula 10 are derivatives of RB represented by Formula 9 as produced by introducing a straight alkyl group $[(CH_2)_{n-1}CH_3)]$, which is the most popular lipophilic group, thereinto.

The RB—Cn—COOH species (Cn being $(CH_2)_n$ and n being the number of carbon atoms contained in the methylene chain) represented by Formula 11 are derivatives obtained by introducing a fatty acid, which is an amphiphilic substituent group. The hydrophilic moiety (COOH) introduced is bound to the terminus of the lipophilic moiety $[(CH_2)_n]$.

On the contrary, the sensitizers for tumor treatment of the invention, namely the RB—COOH—Cn species (Cn being $CH(CH_2)_{n-2}CH_3$ and n being the number of carbon atoms in the alkyl group) represented by Formula 12, are derivatives of RB in which the hydrophilic group (COOH) and lipophilic group $[(CH_2)_{n-2}CH_3]$ introduced are bound to one and the same carbon atom in a side chain of RB.

In the solubility measurement, the respective derivatives having an equal number of carbon atoms in the alkyl group (n=7) were used. The results are shown in Table 3.

TABLE 3

|  | RB | RB—C7 | RB—C7—COOH | RB—COOH—C7 |
|---|---|---|---|---|
| PBS (pH 7.4) | 220 | <0.01 | 1.6 | 0.83 |
| 1-Octanol | <0.1 | 55 | 2.3 | 12 |

(in mmol/l)

As for the solubility in 1-octanol, the three derivatives RB—C7 (corresponding to Formula 10), RB—COOH—C7 (corresponding to Formula 12) and RB—C7—COOH (corresponding to Formula 11) showed values as high as 550 times, 120 times and 23 times the solubility of RB, respectively. The three derivatives each showed a solubility in PBS lower by at least two digits as compared with RB as a result of substituent introduction into one (carboxylate moiety) of the two hydrophilic moieties of RB.

RB (Formula 9) has two hydrophilic moieties, namely carboxylate and oxido ($O^-$). Therefore, as shown in Table 3, its solubility in the aqueous solution [PBS (pH 7.4)] was as high as 220 mmol/L (liter) while its solubility in the organic solvent (1-octanol) was extremely low (<0.1 mmol/L).

Conversely, RB—C7 (Formula 10) obtained by introducing a lipophilic group alone showed the highest solubility in the organic solvent, namely 550 times as compared with RB. However, its solubility in the aqueous solution was the lowest, so that it was almost impossible to prepare a stable aqueous solution for administration in vivo by an ordinary method (cf. Test Example 2).

As for RB—C7—COOH (Formula 11) obtained by introducing an amphiphilic substituent group, the solubility in the aqueous solution was 160 times that of RB—C7 (Formula 10) but the solubility in the organic solvent was only 23 times as that of RB. It is presumable that since the hydrophilic group occurs at the terminus of the alkyl group, which is the lipophilic moiety, the increase in lipophilicity was not so great as expected.

On the other hand, the solubility of RB—COOH—C7 (Formula 12), which is a sonochemical sensitizer according to the invention, in the aqueous solution was 83 times that of RB—C7 and the solubility was at such a level that an aqueous solution for administration in vivo could be prepared in the same manner as with RB—C7—COOH (Formula 11) although it was somewhat inferior as compared with RB—C7—COOH (cf. Test Example 2).

Its solubility in the organic solvent was as high as 120 times that of RB and it was thus found that it has lipophilicity as well. It is believed that since the hydrophilic group (—COOH) and lipophilic group $[(CH_2)_{n-2}CH_3]$ are bound to one and the same carbon atom to thereby form a branched structure, the hydrophilicity and lipophilicity could successfully be manifested simultaneously.

Test Example 2

Preparation of RB solution and RB lipophilic derivative solutions for administration in vivo:

A solution each of RB (Formula 9), RB—Cn—COOH (Formula 11) and RB—COOH—Cn (Formula 12) with a concentration of 10 mg/mL and a solution of RB—Cn (Formula 10) with a concentration of 1 mg/mL were prepared.

RB: 50 mg of RB was dissolved in PBS (pH 7.4) and the whole volume was made 5 mL.

RB—Cn: 4 mg of RB—Cn was dissolved in 0.4 mL of DMSO. Then, 0.4 mL of ethanol, 0.3 mL of 0.1 N NaOH aqueous solution and 1.0 mL of PBS (pH 7.4) were added and, further, 0.1 N hydrochloric acid was added to adjust the pH to about 7.4 and the whole volume was made 4 mL by further adding PBS (pH 7.4). The DMSO accounted for 10% of the whole solution.

RB—C7—COOH: 30 mg of RB—C7—COOH was dissolved in 1.2 mL of 0.1 N NaOH aqueous solution, 0.1 N hydrochloric acid was added to adjust the pH to about 7.4 and the whole volume was made 3 mL by further adding PBS (pH 7.4).

RB—COOH—Cn: n=2 to 10:30 mg of each RB—COOH—Cn was dissolved in 1.2 mL of 0.1 N NaOH aqueous solution, 0.1 N hydrochloric acid was added to adjust the pH to about 7.4 and the whole volume was made 3 mL by further adding PBS (pH 7.4). The DMF accounted for 20% of the whole solution.

n=11 to 20:30 mg of each RB—COOH—Cn was dissolved in 0.6 mL of DMF. Then, 1.2 mL of 0.1 N NaOH aqueous solution was added, 0.1 N hydrochloric acid was added to adjust the pH to about 7.4 and the whole volume was made 3 mL by further adding PBS (pH 7.4).

RB was soluble as it was in PBS (pH 7.4), while RB—Cn having the highest lipophilicity could not be dissolved without adding DMSO and ethanol; it could give only a solution having a concentration one digit lower as compared with RB.

RB—C7—COOH and RB—COOH—Cn (n=2 to 10), each having a carboxy group as the hydrophilic group, were soluble in an alkaline aqueous solution alone. Once dissolved, however, they gave solutions with a pH of about 7.4 upon lowering the pH with the acid.

RB—COOH—Cn species in which n=11 to 20 could not give solutions without using DMF. However, solutions having the same concentration as RB could be prepared. It has been established that DMSO and DMF are nontoxic until the concentration of 20% in aqueous solutions.

From Test Example 1 and Test Example 2, it was revealed that RB—COOH—C7 (Formula 12) of the invention is slightly inferior in solubility in aqueous solution to RB—C7—COOH (Formula 11) but can give an aqueous agent solution for administration in vivo in the same manner as RB—C7—COOH. Furthermore, the solubility of RB—COOH—C7 in the organic solvent was about 5 times that of RB—C7—COOH, suggesting that the hydrophilic group and lipophilic group forming a branched structure are in a state to readily manifesting the respective properties.

Then, for investigating whether the improvement in lipophilicity is connected with actual accumulation in tumor tissues, RB—Cn (Formula 10) and RB—COOH—Cn (Formula 12), which both showed a noticeable improvement in lipophilicity, were administered to tumor bearing mice and the fluorescence resulting from excitation of each agent in those tissues was measured to thereby evaluate the accumulation of the agent in tumor tissues. For comparison, the accumulation of RB in tumor tissues was also evaluated.

Test Example 3

Evaluation of the accumulation of RB—Cn in tumor tissues:

Tumor bearing mice were intravenously administered with RB or RB—Cn and, after the lapse of a predetermined period, tumor tissues were excised. The fluorescence spectrum of the agent extracted from the tumor tissues was measured and the concentration of the agent was estimated from the fluorescence intensity to thereby evaluate the accumulability in tumor tissues. Mice subjected to the test were 5-week male $CDF_1$ mice one to two weeks after subcutaneous implantation of small pieces (e.g. 1 mm$^3$ pieces) of the murine experimental tumor Colone 26. The dose of the agent was 10 mg/kg and methanol or chloroform was used for the extraction.

Figure 2:
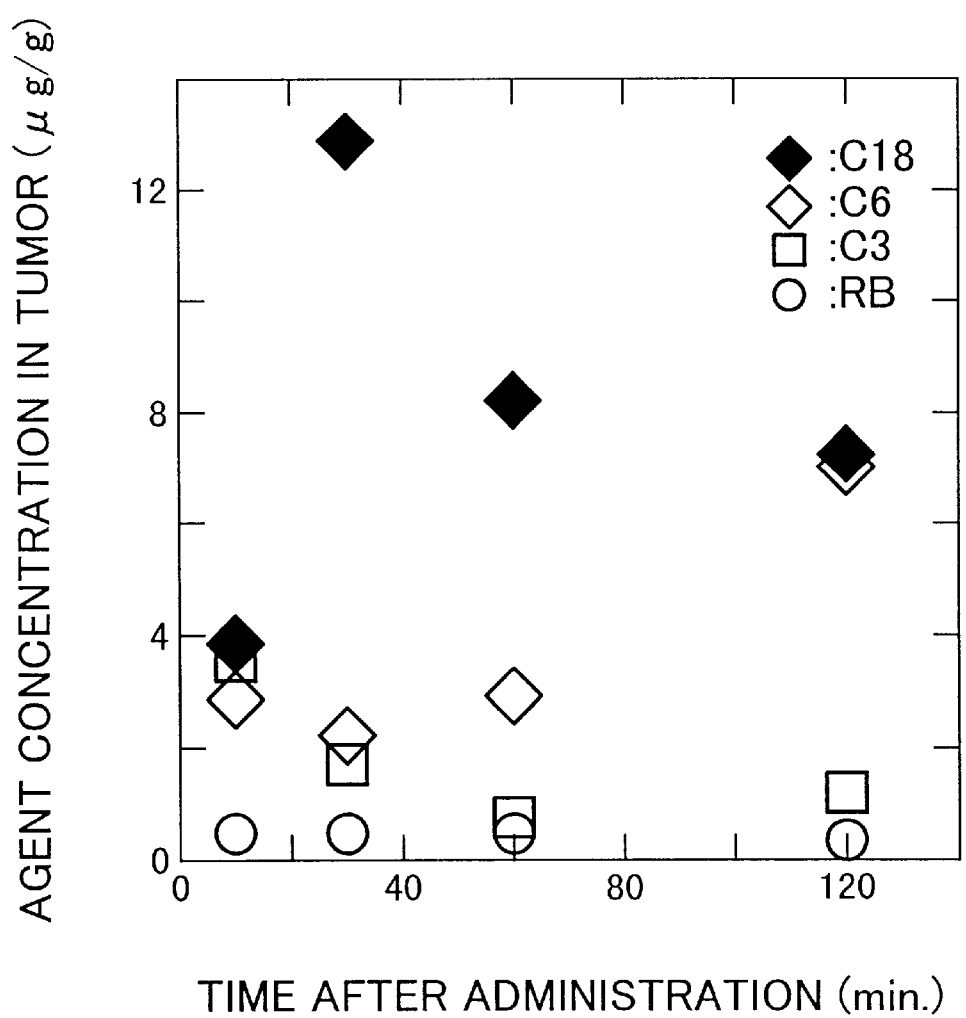
FIG. 2 is a characteristic figure showing the agent concentrations in tumor tissues versus the time after administration of rose bengal (RB) and rose bengal alkyl esters (RB—Cn).

For RB and RB—Cn species containing 3, 6 or 18 carbon atoms in the alkyl group (RB—C3, RB—C6 and RB—C18), the relations between the time from agent administration to mice to tumor tissue excision and the agent concentration in tumor tissues are shown in FIG. 2. While the occurrence of RB in tumor tissues was hardly observed until 120 minutes after agent administration, the concentrations of RB—C3, RB—C6 and RB—C18 in tumor tissues were all higher as compared with RB and that tendency became more and more significant with the increase in the number of carbon atoms in the alkyl group.

Test Example 4

Figure 3:
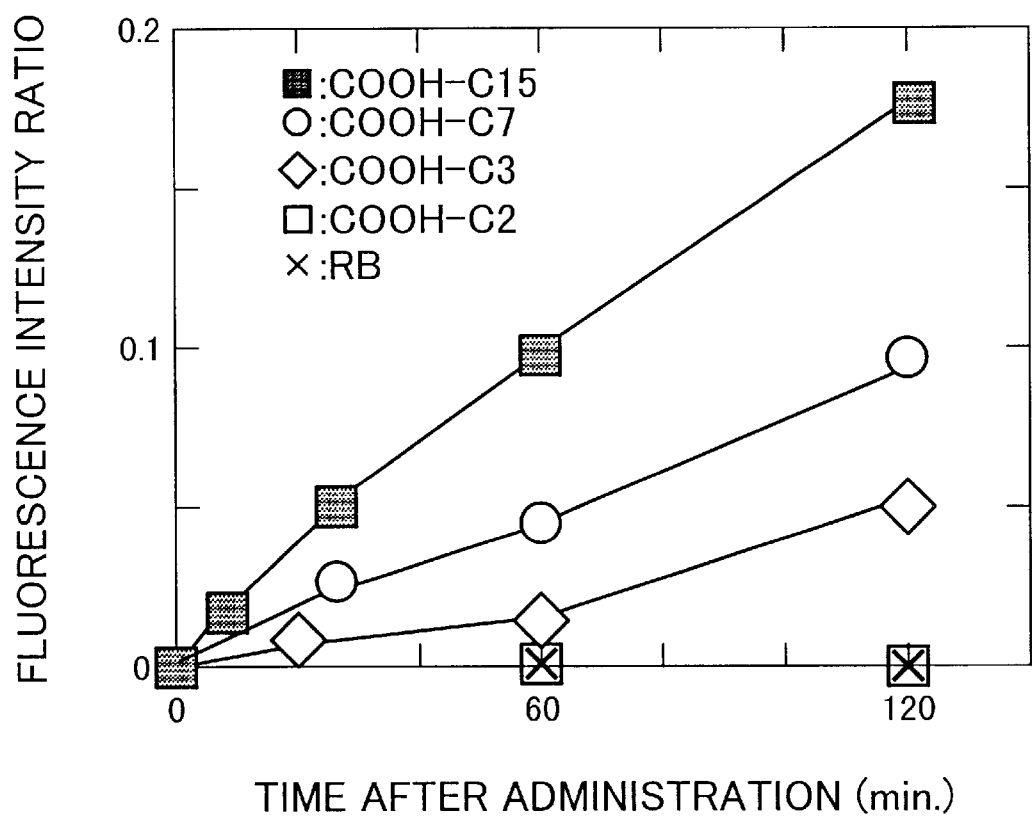
FIG. 3 is a characteristic figure showing the fluorescence intensity ratios of RB and rose bengal-α-carboxyalkyl esters (RB—COOH—Cn) in tumor tissues relative to an internal standard versus the time after administration of the agents.

Evaluation of the accumulation of RB—COOH—Cn in tumor tissues:

Tumor bearing mice were intravenously administered with RB or RB—COOH—Cn and, after the lapse of a predetermined period, tumor tissues were excised. The fluorescence intensity of the tumor tissues was measured and the accumulability in tumor tissues was evaluated based on the ratio of that intensity and the fluorescence intensity of an internal standard (fluorescence intensity ratio). The mice used in the test and the dose of the agent were the same as in Test Example 3. As an example of the results, the relation between the time from agent administration to mice to tumor tissue excision and the fluorescence intensity ratio is shown in FIG. 3 for each of RB and RB—COOH—Cn species containing 2, 3, 7 or 15 carbon atoms in the alkyl group (RB—COOH—C2, RB—COOH—C3, RB—COOH—C7 and RB—COOH—C15).

For RB and RB—COOH—C2, their occurrence in tumor tissues was hardly observed until 120 minutes after agent administration, while the concentrations of RB—COOH—C3, RB—COOH—C7 and RB—COOH—C15 in tumor tissue were all higher than that of RB and the tendency became more significant with the increase in the number of carbon atoms in the alkyl group.

From the above-mentioned Test Example 3 and Test Example 4, it could be confirmed that the accumulability in tumor tissues is improved with the increase in the number of carbon atoms in the alkyl group. Generally, it is considered that an increase in the number of carbon atoms in the straight alkyl group results in an increase in lipophilicity. Presumably, the above result indicates that an improvement in lipophilicity results in an improvement in accumulability in tumor tissues.

As mentioned above, it could be established that the sonochemical sensitizer of the invention is endowed with accumulability in tumor tissues owing to improved lipophilicity. It was also found that the number of carbon atoms in the alkyl chain which leads to a certain extent of accumulability in tumor tissues is desirably not less than 3. Now, the influences of such modification on the characteristics as an ultrasonic sensitizer are described.

Test Example 5

Figure 4:
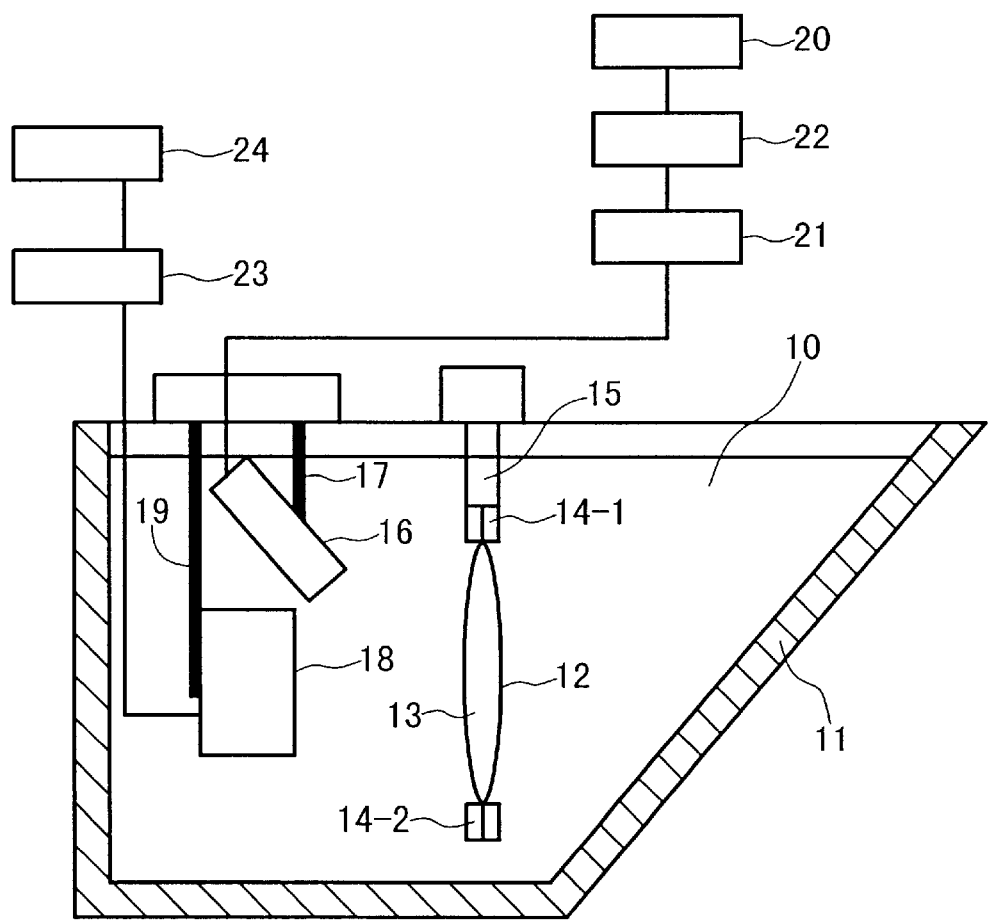
FIG. 4 is a schematic sectional view of an ultrasonic irradiation apparatus for evaluating the acoustic cavitation promoting effect.

Evaluation of the acoustic cavitation promoting effect of RB—Cn:

A 0.1 mmol/L solution of RB—Cn in PBS (pH 7.4, containing 1% DMF) was sealed in a polyethylene bag (30×25 mm, 0.03 mm thick) and irradiated with ultrasonic waves of 0.5 MHz and 1 MHZ simultaneously under conditions of an acoustic intensity of 5 or 10 $W/cm^2$ and an exposure time of 1 minute, using an experimental apparatus having the constitution shown in FIG. 4.

In FIG. 4, 10 indicates degassed water, 11—a water tank, 12—a polyethylene bag, 13—a sample solution, 14-1 and 14-2 each—a holdfast, 15—a hanger, 16—a hydrophone, 17—a supporter, 18—an ultrasound transducer, 19—a supporter, 20—a signal processor, 21—an amplifier, 22—a spectrum analyzer, 23—an amplifier, and 24—a wave generator.

Figure 5:
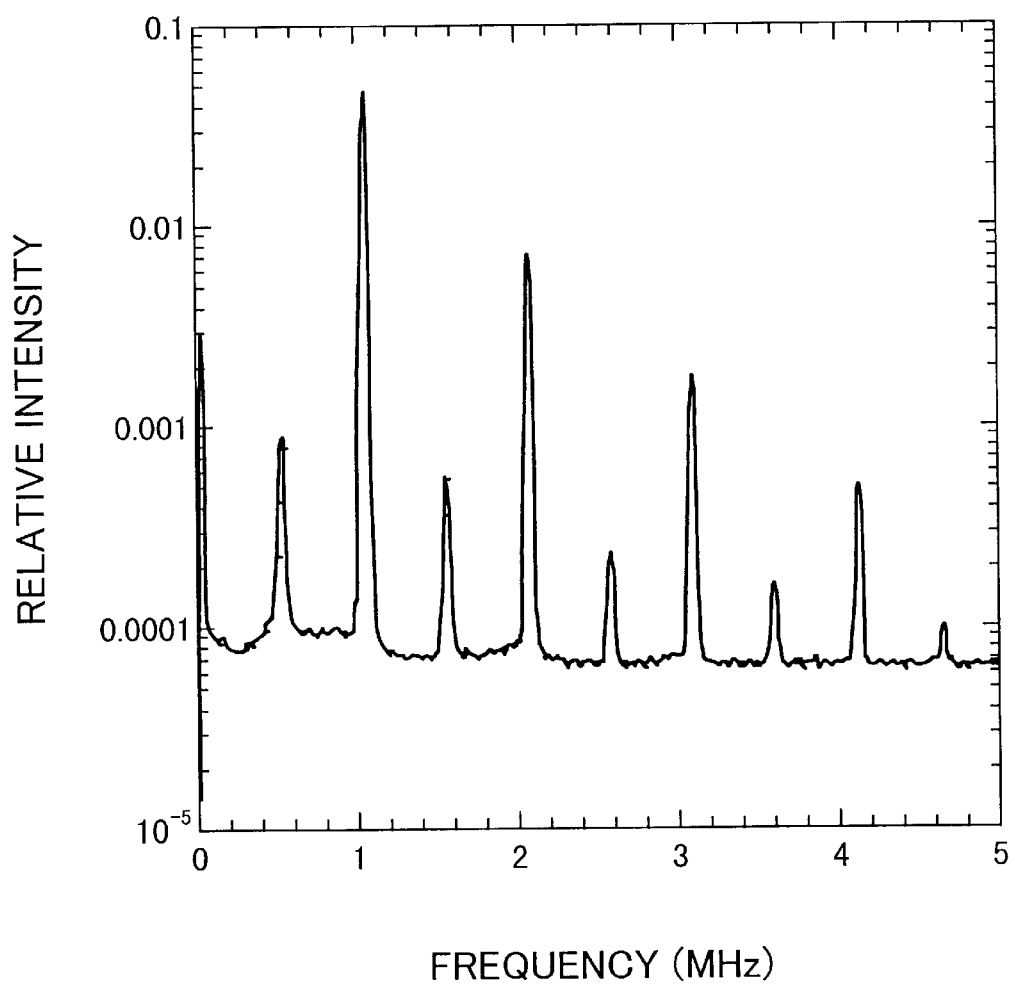
FIG. 5 is a characteristic figure expressing a typical acoustic signal obtained from a sample upon ultrasound irradiation.

The acoustic signals at the subharmonic (250 kHz) characteristic to acoustic cavitation were measured at one-second intervals using a focusing type hydrophone, the root mean square of the signal amplitudes during the irradiation period was calculated and this was used as an indication of acoustic cavitation. A typical acoustic signal pattern obtainable from a sample by ultrasound irradiation is shown in FIG. 5.

Figure 6:
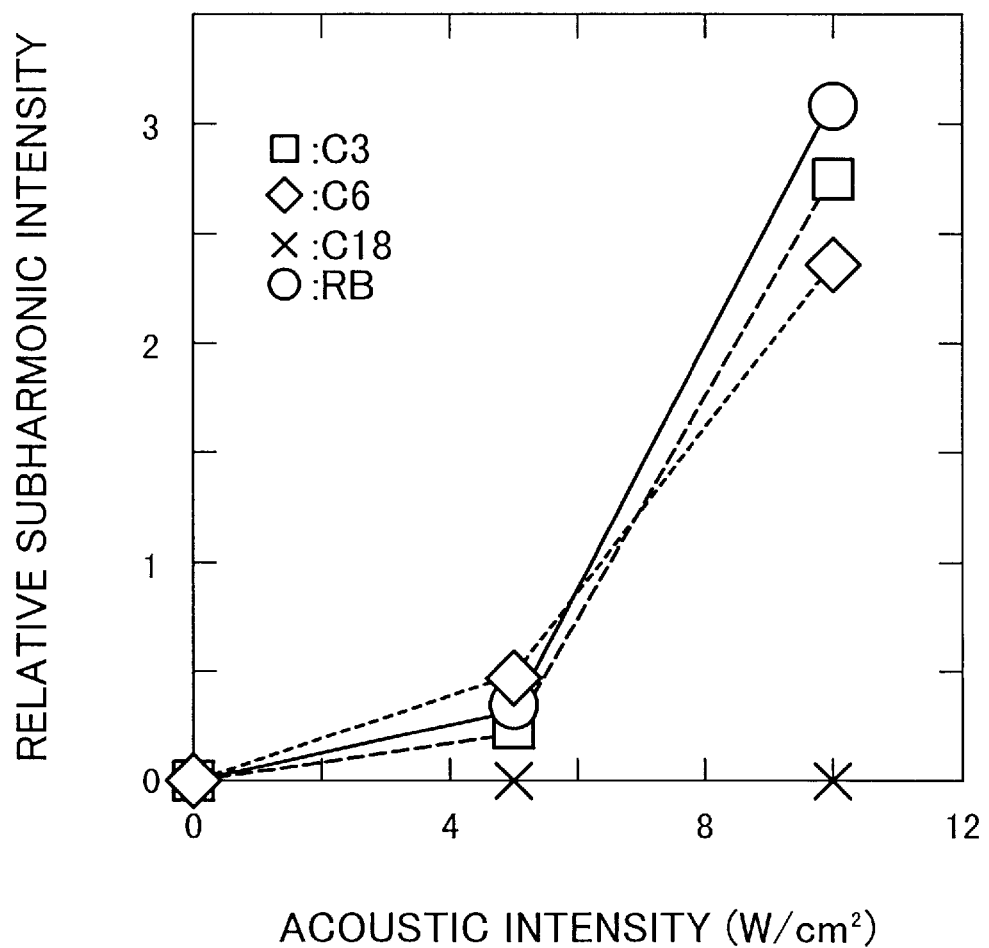
FIG. 6 is a characteristic figure expressing dependence of relative subharmonic intensity on acoustic intensity for RB and RB—Cn.

For comparison, a 0.1 mmol/L solution of RB in PBS (pH 7.4) was also measured for subharmonic signals. It has been confirmed in a preliminary investigation that even when 1% of DMF is contained in the solution, the subharmonic intensity is not influenced. For each of RB and the RB—Cn species containing 3, 6 or 18 carbon atoms in the alkyl group (RB—C3, RB—C6 and RB—C18), the relation between acoustic intensity and subharmonic intensity is shown in FIG. 6.

With RB, RB—C3 and RB—C6, the subharmonic generation was observed at the ultrasound intensity of 5 $W/cm^2$ and the subharmonic intensity increased as the acoustic intensity increased. With RB—C18, however, no subharmonic formation was observed even at the ultrasound intensity of 10 $W/cm^2$.

Test Example 6

Evaluation of the acoustic cavitation promoting effect of RB—COOH—Cn:

Using a 0.1 mmol/L solution of RB—COOH—Cn in PBS (pH 7.4), the acoustic cavitation promoting effect was evaluated in the same manner as in Test Example 5.

Figure 7:
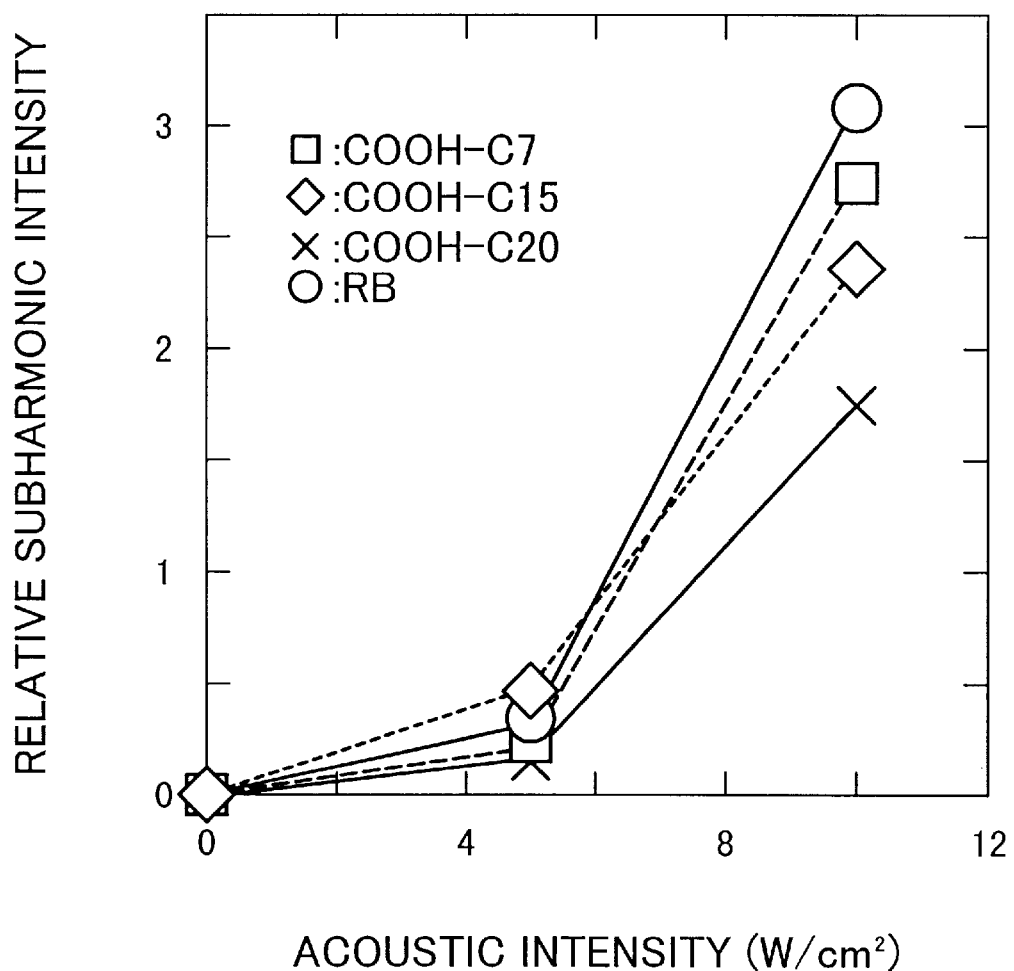
FIG. 7 is a characteristic figure expressing dependence of relative subharmonic intensity on acoustic intensity for RB and RB—COOH—Cn.

As an example of the results, the relation between acoustic intensity and subharmonic intensity is shown in FIG. 7 for each of RB and RB—COOH—Cn species containing 7, 15 or 20 carbon atoms in the alkyl group (RB—COOH—C7, RB—COOH—C15 and RB—COOH—C20).

With all of RB—COOH—C7, RB—COOH—C15 and RB——COOH—C20, the subharmonic generation was observed at the acoustic intensity of 5 $W/cm^2$ and the subharmonic intensity increased with the increase in acoustic intensity.

Test Example 7

Evaluation of the acoustic cavitation promoting effect of xanthene dye sensitizer—COOH—Cn:

Using a 0.1 mmol/L solution of xanthene dye sensitizer—COOH—Cn in PBS (pH 7.4), the acoustic cavitation promoting effect was evaluated in the same manner as in Test Example 5.

Figure 8:
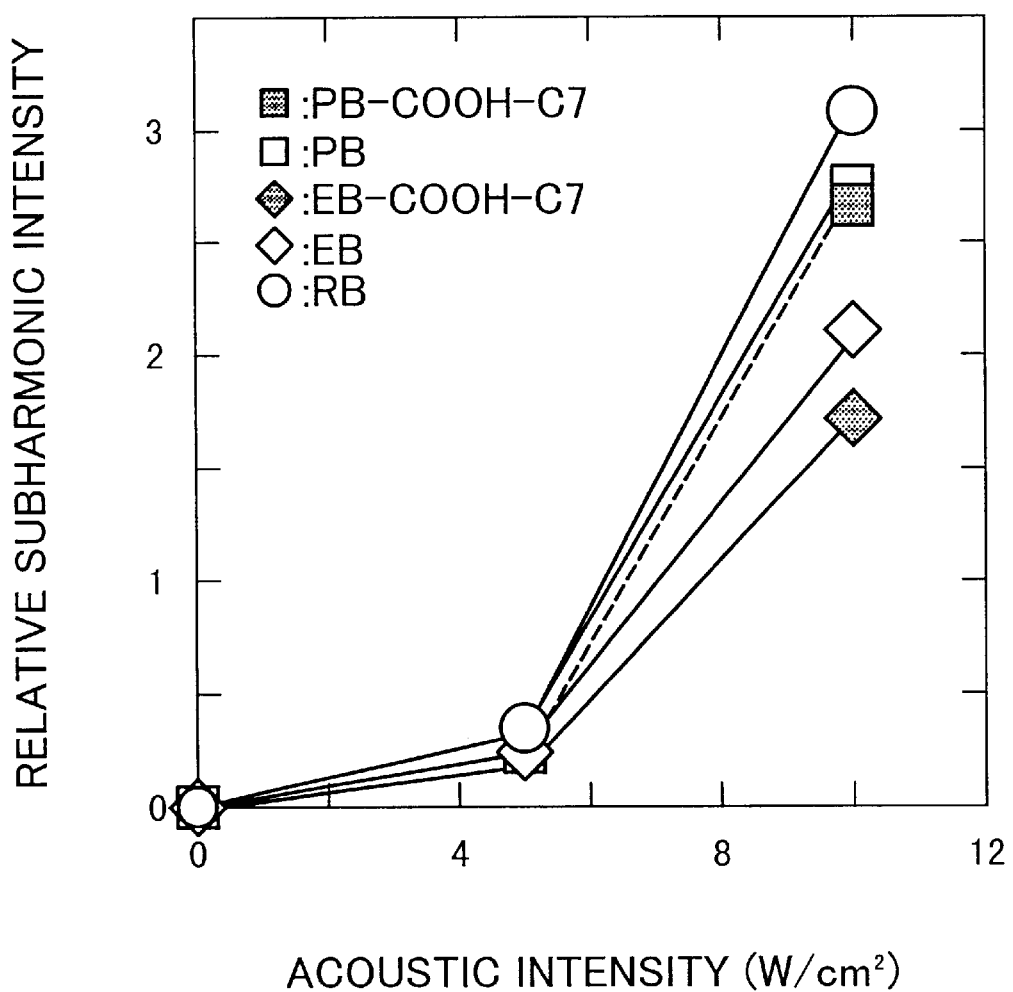
FIG. 8 is a characteristic figure expressing dependence of relative subharmonic intensity on acoustic intensity for some xanthene dye sensitizers and —COOH—Cn derivatives thereof.

As an example of the results, the relation between acoustic intensity and subharmonic intensity is shown in FIG. 8 for each of PB—COOH—C7 and EB—COOH—C7 and the respective starting materials PB and EB. With each compound, the subharmonic generation was observed at the acoustic intensity of 5 $W/cm^2$ and the subharmonic intensity increased with the increase in acoustic intensity.

From Test Examples 5 to 7, it was revealed that, among the RB—Cn species of the type such that the hydrophilic group and lipophilic group are remote within the molecule, those having an excessively large number of carbon atoms in the alkyl group with the balance therebetween excessively shifted to lipophilicity undergo an impairment in the acoustic cavitation promoting characteristic whereas the RB—COOH—Cn species of the invention, which have hydrophilicity as well, retain that characteristic even with the compound containing 20 carbon atoms in the alkyl chain (n=20). It was also confirmed that when other xanthene dye sensitizers other than RB are used as the starting materials, the compounds of the invention equally retain the acoustic cavitation promoting effect of the starting materials.

Then, whether RB—Cn and RB—COOH—Cn retain the ability to reveal an antitumor effect (characteristic 2), which is another characteristic possessed by RB, was examined based on the photosensitivity thereof. The mechanisms of antitumor activity are in agreement with the mechanisms so far supposed in photodynamic therapy and the sonochemical sensitizers so far known all have photosensitizing activity.

Xanthene dye sensitizers are typical photosensitizers and are frequently used particularly in reactions in which singlet oxygen is involved. Therefore, the manifestation of an antitumor effect can be estimated from the retention of the photosensitivity.

Test Example 8

Evaluation of the photosensitivity of RB—Cn:

The photo-oxidation reaction of iodide as represented by Equation 4 was carried out in the presence of RB—Cn and the photosensitivity of the compound was evaluated.

$$2I^- \rightarrow I_2, I_2 + I^- \rightarrow I_3^- \qquad (4)$$

A mixed solution composed of 2 mL of a 0.1 mol/L solution of potassium iodide in DMF and 1 mL of a 1 mmol/L solution of RB—Cn in DMF was placed in a glass dish (48 mm in diameter) and irradiated with light of 365 nm for a predetermined period. The absorbance, at 350 nm, of the sample was measured before and after exposure. 350 nm is the absorption maximum wavelength of $I_3^-$. Based on the absorbance (A), the concentration of $I_3^-$ was calculated using Equation 5.

$$\epsilon = (1/77) \; mmol \cdot A \qquad (5)$$

Figure 9:
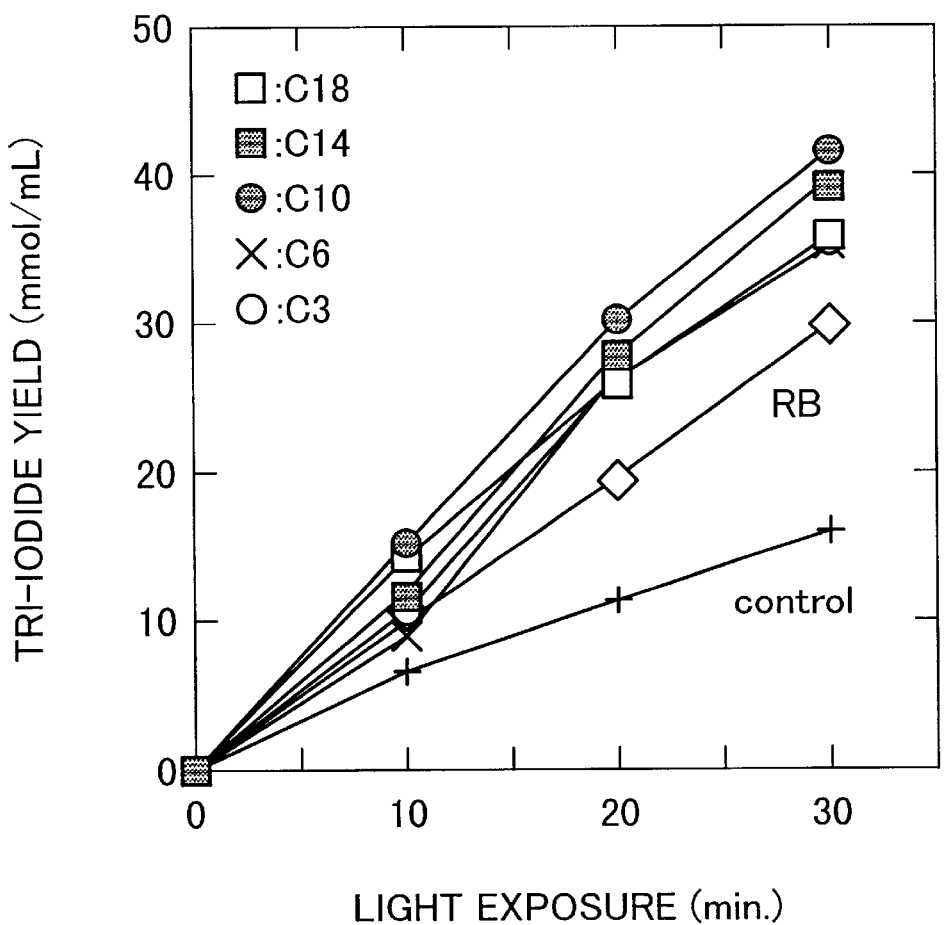
FIG. 9 is a characteristic figure expressing the yields of products versus the light exposure time in the photo oxidation of iodide in the presence of RB or RB—Cn.

The relation between the light exposure time and yield in the photo-oxidation reaction of iodide carried out in the presence of RB or RB—Cn containing 3, 6, 10, 14 or 18 carbon atoms in the alkyl group (RB—C3, RB—C6, RB—Cl0, RB—Cl4, RB—Cl8) is shown in FIG. 9. In each case, the yield was almost proportional to the exposure time.

As compared with the case in which no agent was added (control), the yield in the presence of RB or RB—Cn was about 2 to 3 times when the exposure time was 30 minutes. On comparison between RB and RB—Cn, the yield in the presence of RB—Cn was about 1.2 to 1.4 times, namely slightly higher, as compared with RB for the exposure time of 30 minutes. Comparison of RB—C3 to RB—C18 revealed no regularity in the relation between the number of carbon atoms in the alkyl group and the yield for the numbers of carbon atoms of 3 to 18.

Test Example 9

Evaluation of the photosensitivity of RB—COOH—Cn:

The procedure of Test Example 8 was followed in the presence of RB—COOH—Cn.

Figure 10:
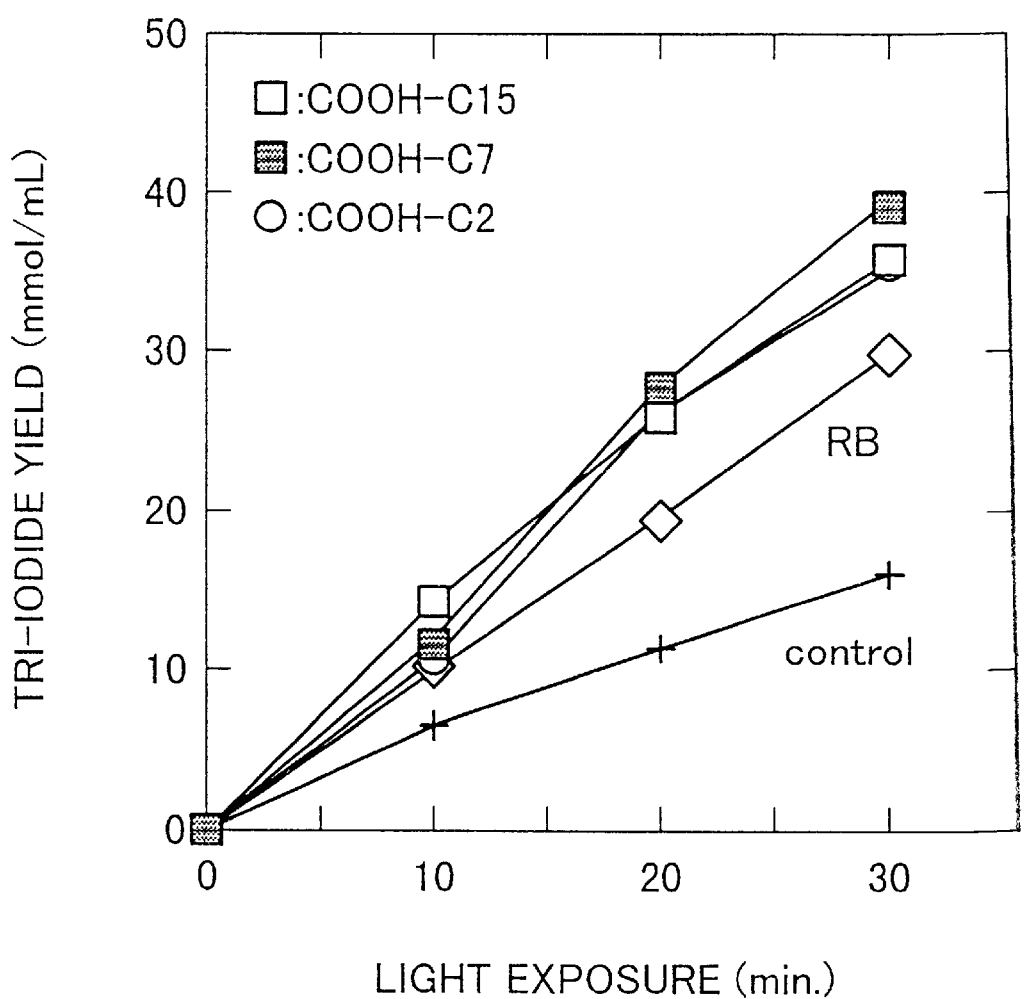
FIG. 10 is a characteristic figure expressing the yields of products versus the light exposure time in the photo oxidation of iodide in the presence of RB or RB—COOH—Cn.

As an example of the results, the relation between the exposure time and yield in the photo-oxidation reaction of iodine carried out in the presence of RB or RB—COOH—Cn containing 2, 7 or 15 carbon atoms in the alkyl group (RB—COOH—C2, RB—COOH—C7, RB—COOH—C15) is shown in FIG. 10. In each case, the yield was almost proportional to the exposure time.

As compared with the case in which no agent was added (control), the yield in the presence of RB or RB—COOH—Cn was about 2 to 3 times when the exposure time was 30 minutes.

On comparison between RB and RB—COOH—Cn, the yield in the presence of RB—COOH—Cn was slightly higher as compared with RB for the exposure time of 30 minutes. Comparison of RB—COOH—C2 to RB—COOH—Cl5 revealed no regularity in the relation between the number of carbon atoms in the alkyl group and the yield for the numbers of carbon atoms of 2 to 15.

From Test Example 8 and Test Example 9 mentioned above, it was found that yield of the product in the above photo-oxidation reaction is higher in the presence of RB—Cn or RB—COOH—Cn as compared with the control and is comparable to the case of RB. No regularity was found in the relation between the number of carbon atoms in the alkyl group and the yield.

From the above results, it is presumable that either the introduction of lipophilic group only or the introduction of hydrophilic and lipophilic groups of the types of the present invention will not influence the photosensitivity, hence will not influence the antitumor effect revealing characteristic, either.

As demonstrated in the above test examples, the compounds of the invention which has a structure such that a hydrophilic group and a lipophilic group are branching from one and the same carbon atom are compounds endowed with accumulability in tumor tissues without impairing the characteristics of the original sensitizers.

Example 5

In this example, an example of the ultrasonic treatment system in which the xanthene-dye-structure-containing sensitizer shown in each of the above examples is used as an ultrasonic contrast agent and as a sonochemical sensitizer.

Figure 11:
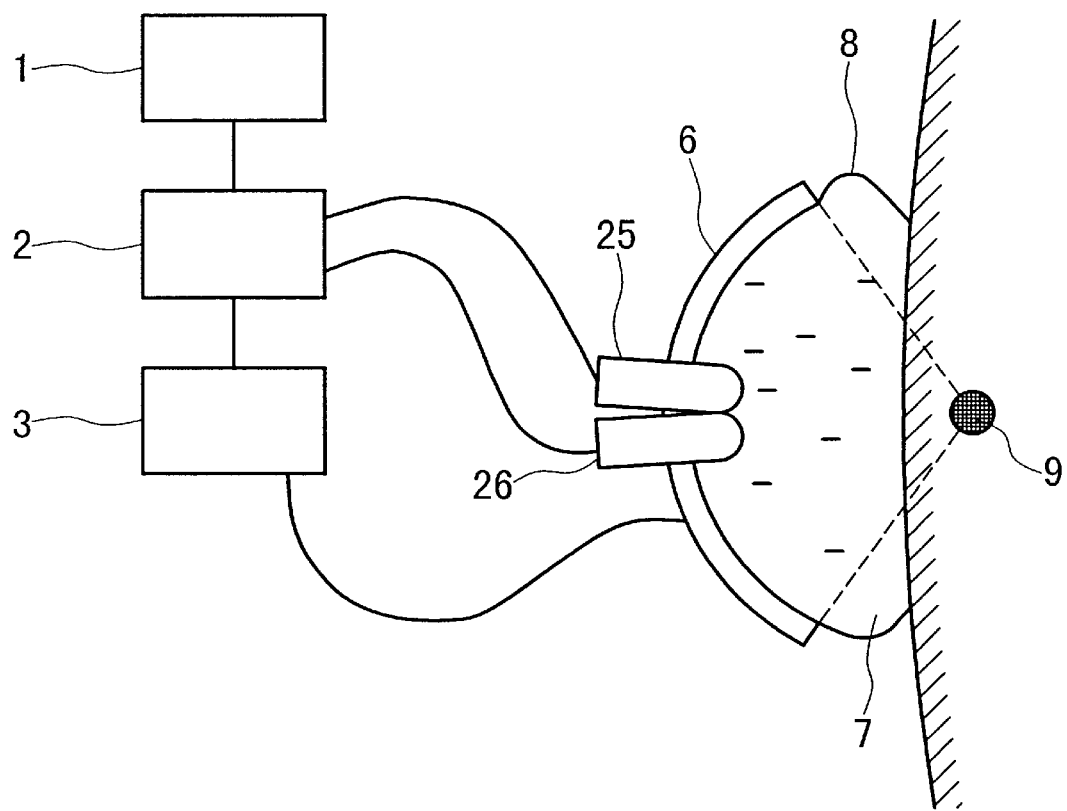
FIG. 11 is a schematic representation of the ultrasonic treatment system according to an embodiment of the invention.

Referring to FIG. 11, which is a schematic representation of the ultrasonic treatment system of the invention, the system is described. The system comprises a monitor 1, a controller 2, a wave generator and amplifier 3, an ultrasonic transducer 25 for generating bubbles, an ultrasonic imaging probe 26, an ultrasonic therapeutic transducer 6, and a matching layer 8 containing degassed water 7. The controller 2 is constituted so that the focus of the ultrasonic therapeutic transducer 6 can be adjusted based on the diagnostic ultrasonic image obtained through the ultrasonic imaging probe 26.

The ultrasonic transducer 25 for generating bubbles is constituted using a piezoelectric device for 0.1 to 4 MHz and is constituted so that pulsed waves and continuous waves of not less than 1 ms can be generated. The ultrasonic imaging probe 26 is not particularly restricted but, in many instances, one sensitive to those frequencies suited for the target 9 for treatment as selected from the frequency range of 3 to 10 MHz, in particular, is used. The ultrasonic therapeutic transducer 6 is constituted so that ultrasound can be generated by means of the piezoelectric device for the resonance frequency of 0.5 to 4.5 MHz.

The system is constituted to allow the following procedure. In the step of ultrasound irradiation for treatment, the target 9 for treatment is first irradiated with ultrasound for imaging, the focus of the ultrasonic therapeutic transducer 6 is then adjusted by means of the controller 2 based on the diagnostic ultrasonic image obtained by the ultrasonic imaging probe 26, and the target 9 for treatment with xanthene-dye-structure-containing sensitizer of the invention administered in advance is irradiated with ultrasound by means of the ultrasonic transducer 25 for generating bubbles for generation of bubbles (acoustic cavitation) stabilized by the xanthene-dye-structure-containing sensitizer of the invention. And, the diagnostic ultrasonic image as contrasted by the bubbles and detected by the ultrasonic imaging probe 26 is displayed on a display device (not shown) and, after confirmation of the target 9 for treatment, the target 9 for treatment is irradiated with therapeutic ultrasound by means of the ultrasonic therapeutic transducer 6.

By extracorporeally generating stabilized bubbles beforehand by blending the xanthene-dye-structure-containing sensitizer with a gas, such as air, by shaking, for instance, it is also possible to produce an effect comparable to the bubble generation by the ultrasonic transducer 25 for generating bubbles.

The modality of ultrasonic therapy according to the present invention comprises the step of irradiating a target for treatment in vivo with the ultrasound for imaging as generated from an ultrasonic imaging probe to thereby obtain a diagnostic ultrasonic image of the target for treatment, the step of adjusting the intensity and/or focus of the therapeutic ultrasound as generated from an ultrasonic therapeutic transducer based on the diagnostic ultrasonic image, the step of irradiating the target for treatment with administered sensitizer for tumor treatment beforehand with the ultrasound generated by an ultrasonic transducer for generating bubbles to thereby generate bubbles, which are stabilized by the sensitizer for tumor treatment, by ultrasound irradiation, the step of displaying the diagnostic ultrasonic image obtained by the ultrasonic imaging probe and contrasted by the bubbles and the step of irradiating the target for treatment with the therapeutic ultrasound after displaying of the diagnostic ultrasonic image as contrasted by the bubbles, in which modality (1) the sensitizer for tumor treatment contains a xanthene dye structure and has a structure such that a hydrophilic group and a lipophilic group are bound to one and the same carbon atom within the molecule and, more particularly, (2) the sensitizer for tumor treatment has the chemical formula of Formula 1 in which X and Y each is a halogen atom or a hydrogen atom, Z is an alkali metal atom or a hydrogen atom, R1 is a lipophilic group, R2 is a hydrophilic group and R3 is a lipophilic group R1 or a hydrophilic group R2 or a hydrogen atom, the above compound being characterized in that it contains a xanthene dye structure and can enhance the effect of tumor treatment as produced by ultrasound irradiation.

The sonochemical sensitizer to be used in the modality of ultrasonic therapy according to the invention has a structure such that a lipophilic group and a hydrophilic group are bound to one and the same carbon atom of a xanthene-dye-structure-containing compound; it is high in selectivity for tumor tissues and enables the treatment of malignant tumor using ultrasound.

Test Example 10

Evaluation of RB—COOH—Cn for bubble stability:

Using a 0.1 mmol/L solution of RB—COOH—C7 in PBS (pH 7.4), the stability of bubbles was measured. 4 mL of the solution of RB—COOH—C7 was placed in a test tube having a length of about 12 mm and shaken on a shaker for 5 minutes and then the time until the disappearance of the bubbles was measured. PBS was used as a control. While PBS could hardly stabilize bubbles, RB—COOH—C7 allowed bubbles to remain for about 120 seconds after shaking and thus was found to have a bubble-stabilizing effect.

Test Example 11

Evaluation of RB—COOH—Cn for contrast-enhancing effect:

Using an ultrasound diagnostic system equipped with a linear probe with a central frequency of 5 MHz, 5 mL of the solution of RB—COOH—C7 obtained in Test Example 10 was intravenously administered to a dog (weighing 12 kg, 2 years old) while ultrasonically scanning the hepatic region of the dog with mode B. Immediately thereafter, 5 mL of physiological saline was administered. After administration, the hepatic artery and aorta were imaged and the imaging lasted for about 30 seconds.

As illustrated hereinabove in detail, the present invention has accomplished the objects pursued, namely to provide a xanthene-dye-structure-containing-sonochemical sensitizer which is accumulable in tumor tissues (3)) without impairing the two following characteristics, (1) promoting acoustic cavitation and (2). This sensitizer is highly selective for tumor tissues and can enhance the effect of tumor treatment and makes it possible to effectively carry out the treatment of malignant tumor using ultrasound.

Further, according to the invention, it is possible to effect imaging in obtaining diagnostic ultrasonic images to thereby provide treatment more effectively.

What is claimed is:

1. A sensitizer for tumor treatment by ultrasound radiation, said sensitizer having a structure shown by FORMULA 1:

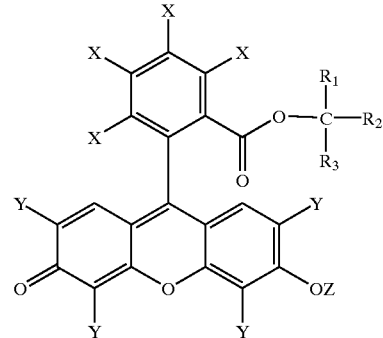

FORMULA 1 wherein X and Y each is a halogen atom or a hydrogen atom, Z is an alkali metal atom or a hydrogen atom, R1 is a lipophilic group, R2 is a hydrophilic group and R3 is a lipophilic group or a hydrophilic group or a hydrogen atom.

2. The sensitizer for tumor treatment as claimed in claim 1, wherein X and Y each is a halogen atom and Z is an alkali metal atom.

3. The sensitizer for tumor treatment as claimed in claim 1, wherein said lipophilic group R1 comprises a straight chain alkyl group having 3 to 30 carbon atoms.

4. The sensitizer for tumor treatment as claimed in claim 1, wherein said lipophilic group R1 is selected from the group consisting of an alkyl group, a first group derived from the alkyl group by having a carbon—carbon double bond substituted for a carbon—carbon single bond of the alkyl group, a second group derived from the alkyl group by having a carbon—carbon triple bond substituted for a carbon—carbon single bond of the alkyl group, a third group derived from the alkyl group by having a phenyl group bound to the terminus of the alkyl group, a fourth group derived from the alkyl group by having an ether linkage substituted for a carbon—carbon single bond of the alkyl group, a fifth group derived from the alkyl group by having an ester linkage substituted for a carbon—carbon single bond of the alkyl group, a sixth group derived from the alkyl group by having an amido linkage substituted for a carbon—carbon single bond of the alkyl group, and a seventh group derived from the alkyl group by having a sulfur linkage substituted for a carbon—carbon single bond of the alkyl group.

5. The sensitizer for tumor treatment as claimed in claim 1, wherein said hydrophilic group R2 is selected from the group consisting of a carboxy group, a soluble salt of the carboxyl group, a sulfonic acid group, a soluble salt of the sulfonic acid group, a sulfuric acid ester group, a soluble salt of the sulfuric acid ester group, a hydroxy group, a soluble salt of the hydroxy group, an amine group, a soluble salt of the amine group, a quaternary ammonium group, a soluble salt of the quaternary ammonium group, a phosphoric acid group and a soluble salt of the phosphoric acid group.

6. The sensitizer for tumor treatment as claimed in claim 1, wherein said hydrophilic group R2 is a carboxyl group and said lipophilic group R1 is a straight chain alkyl group.

7. The sensitizer for tumor treatment as claimed in claim 1, wherein said hydrophilic group R2 is a carboxyl group, said lipophilic group R1 is a straight chain alkyl group and R3 is a hydrogen atom.

8. The sensitizer for tumor treatment as claimed in claim 1, said lipophilic group R1 comprises a straight chain alkyl group having 3 to 20 carbon atoms.

* * * * *